(12) United States Patent
Maxwell et al.

(10) Patent No.: US 9,539,063 B2
(45) Date of Patent: Jan. 10, 2017

(54) ENDODONTIC ROTARY INSTRUMENTS MADE FROM HOLLOW TUBES AND METHODS OF MANUFACTURING THEREOF

(75) Inventors: Randall Maxwell, Broken Arrow, OK (US); Vincent Shotton, Broken Arrow, OK (US); Kevin Wilkinson, Bixby, OK (US); Yong Gao, Broken Arrow, OK (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/404,570

(22) Filed: Feb. 24, 2012

(65) Prior Publication Data

US 2012/0219927 A1 Aug. 30, 2012

Related U.S. Application Data

(60) Provisional application No. 61/446,314, filed on Feb. 24, 2011, provisional application No. 61/446,251, filed on Feb. 24, 2011.

(51) Int. Cl.
*A61C 5/02* (2006.01)
*H01J 9/02* (2006.01)

(52) U.S. Cl.
CPC .............. *A61C 5/023* (2013.01); *H01J 9/025* (2013.01); *Y10T 29/49567* (2015.01)

(58) Field of Classification Search
None
See application file for complete search history.

(56) References Cited

U.S. PATENT DOCUMENTS

| | | |
|---|---|---|
| 4,276,880 A | 7/1981 | Malmin |
| 5,941,760 A | 8/1999 | Heath et al. |
| 6,107,004 A | 8/2000 | Donadio, III |
| 6,162,202 A | 12/2000 | Sicurelli et al. |
| 6,368,107 B2 | 4/2002 | Danger et al. |
| 6,890,134 B1 | 5/2005 | Wagner et al. |
| 7,713,059 B2 | 5/2010 | Hof et al. |
| 2005/0154446 A1* | 7/2005 | Phillips et al. .............. 623/1.13 |
| 2007/0054238 A1* | 3/2007 | Hof et al. ..................... 433/102 |
| 2010/0028830 A1 | 2/2010 | Hof |

FOREIGN PATENT DOCUMENTS

| | | |
|---|---|---|
| FR | 1163169 | 9/1958 |
| JP | 8103456 | 4/1996 |
| WO | 2009137815 A1 | 11/2009 |

* cited by examiner

*Primary Examiner* — Shamim Ahmed
*Assistant Examiner* — Bradford Gates
(74) *Attorney, Agent, or Firm* — David A. Zdurne; Douglas J. Hura; Leona Levin

(57) ABSTRACT

A method for manufacturing a hollow instrument comprising the steps of: providing a hollow tube having a longitudinal tube axis; forming at least one opening along a shaft portion of the hollow tube following a predetermined pattern thereby defining a plurality of fingers; and deforming at least a portion of the hollow tube into a desired shape; and optionally joining at least two fingers along a portion of the opening to secure the hollow tube in the desired shape thereby forming the hollow instrument.

13 Claims, 19 Drawing Sheets

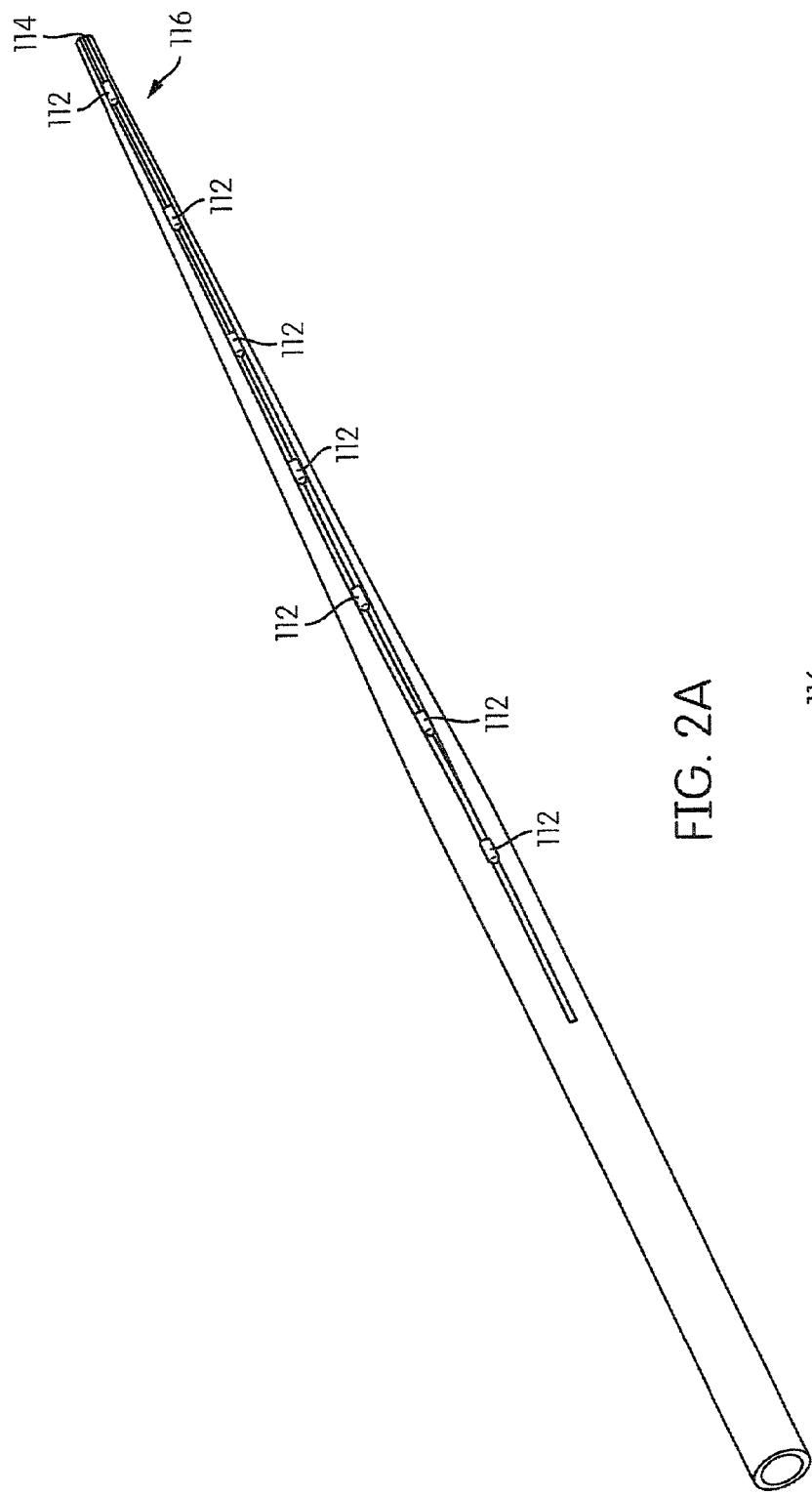
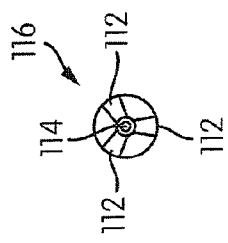

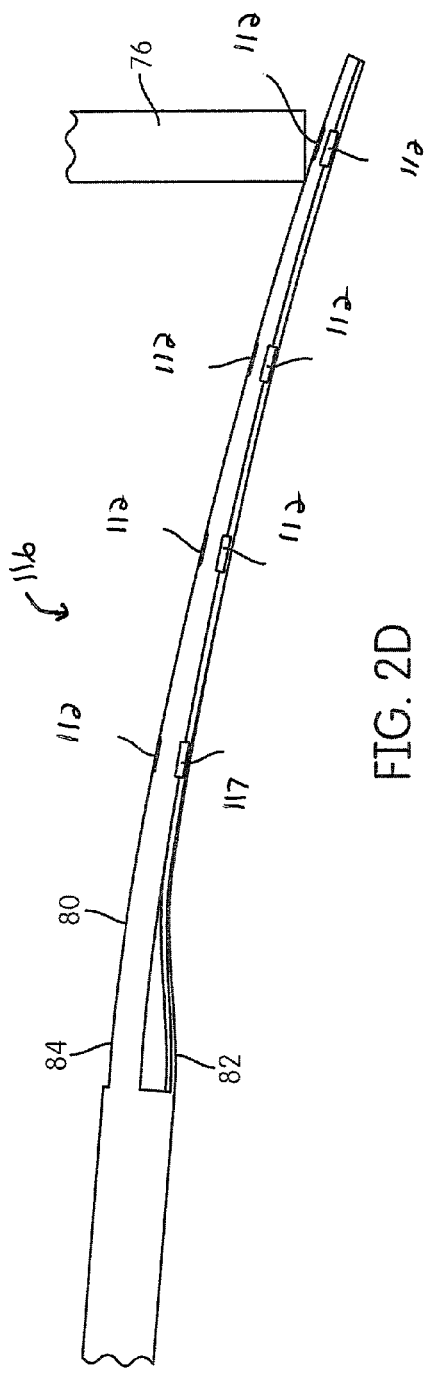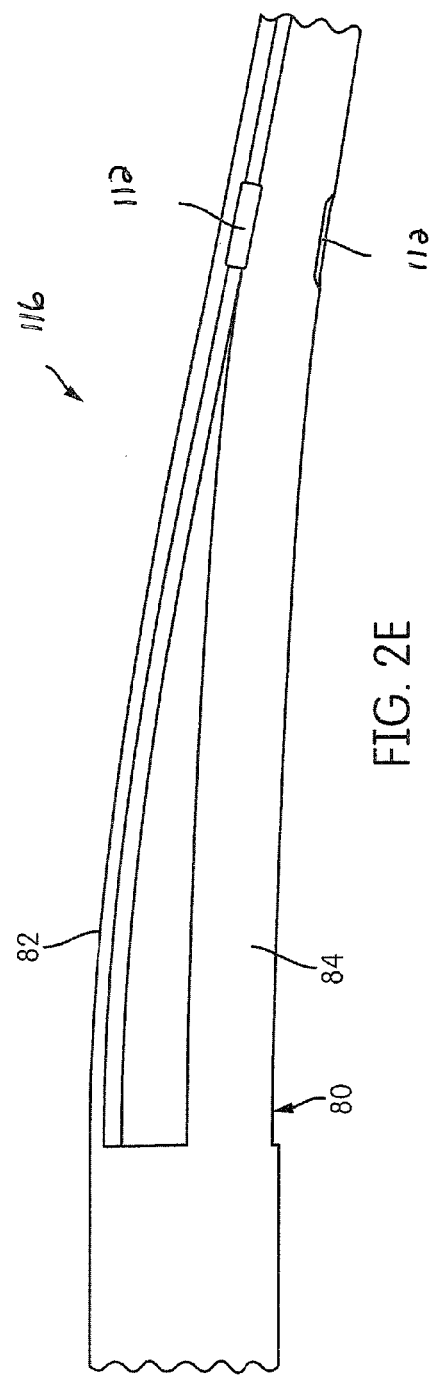

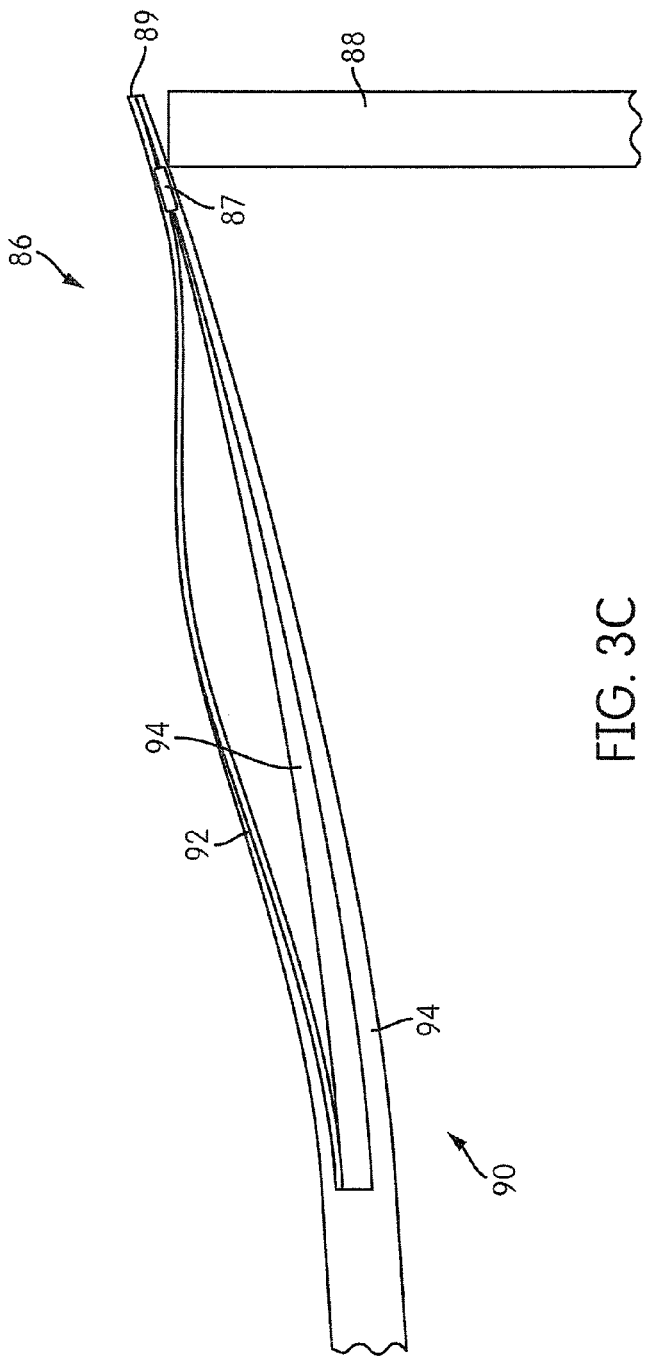
FIG. 3B
FIG. 3C

US 9,539,063 B2

ENDODONTIC ROTARY INSTRUMENTS MADE FROM HOLLOW TUBES AND METHODS OF MANUFACTURING THEREOF

RELATED DOCUMENTS

This application claims the benefit of priority U.S. provisional application Ser. No. 61/446,251, filed Feb. 24, 2011 and U.S. provisional application Ser. No. 61/446,314, filed Feb. 24, 2011, which are herein incorporated by reference for all purposes.

FIELD OF INVENTION

The present invention is directed to a method for manufacturing a dental instrument, and specifically to a rotary file useful for shaping and cleaning root canals.

BACKGROUND OF THE INVENTION

U.S. Pat. No. 7,713,059 discusses an instrument used for cleaning and/or shaping a channel that exists in or through a solid object. It is designed to shape the channel 3 dimensionally by having the outer contour change as a result of the forces exerted upon it. The downside to this design is that it can only be used with a motor driving the design up and down along the axis of the object. Furthermore, this design does not rotate. For endodontic applications, a majority of the motors available in the dentist office only has rotation ability. This causes the doctor to invest in a new motor. Also, the ability of this design to perform a cut is allowed by changing the surface texture (i.e. roughening the outer surface) to engage and cut into the material (e.g., shaving the root canal at a high speed as it changes shape). Lastly, the method of manufacturing this design is very similar to stents made for the cardiovascular industry where a laser cut of a cylindrical tube is created, which is a very time consuming and costly process. Therefore, the cost of the instrument is much higher than conventional rotary file instruments (approximately 7 times higher).

U.S. Pat. Nos. 6,890,134 and 5,941,760 generally discuss the common process of manufacturing an endodontic rotary file through a grinding procedure. U.S. Pat. No. 6,368,107 shows a design of having a crossing pattern which is similar to the design being shown in the application but the process they have described would not allow the rotary file to change geometry as a result of the forces exerted upon it.

SUMMARY OF THE INVENTION

The present invention provides an improved endodontic instrument, and/or method for making an endodontic instrument. In one aspect of the present invention, the method for manufacturing the endodontic instruments (e.g., rotary file) from a hollow core portion (e.g., a tube, cylinder, or otherwise). In another aspect of the present invention, the endodontic instrument may incorporate a straight taper, a varied taper, or any combination thereof (e.g., from the tip portion of the instrument to the shank portion of the instrument or portions therebetween).

In another aspect of the present invention is to provide a new rotary instrument design that is able to change the outer contour of a root canal based on the forces exerted upon it. In doing so, may enable this new design to be used in a traditional rotary application such that the dentist may not have to purchase a new motor. In another aspect of the present invention, the new design may not require the addition of roughened surfaces to create a cutting edge. In another aspect of the present invention, this new method of manufacturing may be employed through a photochemical machining process. In another aspect of the present invention, the design may have a variable cross-section through the ribs thus creating an aggressive outer surface for cutting, but optionally a thicker more stable surface for the inside. In another aspect of the invention, the method for manufacturing the new rotary file design may comprise one at least of: providing a sheet (e.g., flat sheet) of Nitinol, Stainless, other material, or combinations thereof (e.g., to be photochemically machined); stamping the sheet to the desired geometry based on the finished file design; rolling the stamped (flat) sheet into the finished geometry; welding (e.g., laser or otherwise type welding) (e.g., at the seam) to complete the finished part; and combination thereof. This process is much less expensive but still allows the benefits of a compressible rotary file.

In another aspect, the present invention contemplates a method for manufacturing a hollow instrument comprising the steps of: providing a hollow tube having a longitudinal tube axis; forming at least one opening along a shaft portion of the hollow tube following a predetermined pattern thereby defining a plurality of fingers; and deforming at least a portion of the hollow tube into a desired shape; and optionally joining at least two fingers along a portion of the opening to secure the hollow tube in the desired shape thereby forming the hollow instrument.

In another aspect, the present invention contemplates a method for manufacturing a hollow instrument comprising the steps of: providing a sheet of material; chemically milling the sheet to form a plurality of openings by remove material following a predetermined pattern, the milled sheet having at least two opposing edges; rolling the milled sheet into a desired tubular geometry; and joining a portion of the at least two opposing edges to secure the desired tubular geometry thereby forming the hollow instrument.

In another aspect, the present invention contemplates a hollow instrument comprising a tube axis, a proximal end and a tip with a shaft portion therebetween; the shaft portion defining a hollow void at least partially bounded by a plurality of fingers and a plurality of longitudinal spacings, each finger extending from the proximal end, wherein the plurality of fingers converge at the tip such that there is contact between at least two fingers for joining to one another by at least one binding.

In another aspect, the present invention contemplates a hollow instrument comprising a tube axis, a proximal end and a tip with a shaft portion therebetween; the shaft portion defining a hollow void at least partially bounded by a matrix of channels and a plurality of openings therebetween, the matrix extending from the proximal end and converges at the tip, wherein the channels extends is a opposing spiral orientations thereby crossing one to form the plurality of openings.

In yet another aspect, any of the aspects of the present invention may be further characterized by one or any combination of the following features: a plurality of longitudinal openings are formed along the shaft portion of the hollow tube defining at least three fingers radially spaced from the tube axis; a first longitudinal opening extends between a first finger and a second finger, a second longitudinal opening extends between the second finger and a third finger, and a third longitudinal opening extends between the third finger and the first finger; during the deforming step the at least two fingers are converged towards the tube axis thereby forming a tapered shaft portion; each of the at least two fingers include an end portion, the end portions being brought into contact during the deforming step to forming a tip of the tapered shaft portion; during the joining step, the first finger is joined to the second finger through a portion of the first longitudinal opening by at least one binding, the second finger is joined to the third finger through a portion of the second longitudinal opening by at least one binding, and the third finger is joined to the first finger through a portion of the third longitudinal opening by at least one binding; each of the at least two fingers are joined to an adjacent finger through at least one of the plurality of longitudinal openings by at least one binding at the tip of the tapered shaft portion; a plurality of bindings join at least two of the first finger, the second finger and the third finger through at least one of the first longitudinal opening, the second longitudinal opening, and the third longitudinal opening; at least one finger includes a plurality of boss portions; further comprising the step of coating or bonding abrasive material to an external surface of the hollow instrument; further comprising the step of cutting the milled sheet to a desired shape; the chemically milling step is accomplished by photochemical machining; the predetermined pattern defines a matrix formed of the plurality of openings that are at least partially bound by channels having an angled exterior surface; at least one finger includes, a plurality of boss portions; the plurality of fingers include opposing side walls, each opposing side wall having a plurality of boss portions; upon the at least two free ends coming into contact, the plurality of boss portions of a first finger and the plurality of boss portions of the second finger are positioned in a staggered relationship such that a boss portion of the first finger is positioned between two boss portions of the second finger; the plurality of fingers include a transverse width that decreases towards the tip of the shaft; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

BRIEF DESCRIPTION OF THE DRAWINGS

FIG. 2A is a perspective view of one embodiment of the present invention that resulting from the semi-finished hollow instrument shown in FIGS. 1A-1C. The finished hollow instrument includes a plurality of deformed fingers that converge towards the tube axis e.g., (file axis) at the tip. After deformation of the fingers, the adjacent fingers are joined through the longitudinal spacing therebetween by multiple bindings (e.g., welds) thereby securing the deformed fingers to provide a typical endodontic rotary file taper. The joining of the fingers are provided at several locations along the taper. The individual finger welds can be at the same distance from the tip creating a symmetrical file or at different distances creating an asymmetrically flexible file. Welds reduce the flexibility of the file locally. Generally more bindings (e.g., welds) result in less flexibility of the endodontic instrument.

FIG. 2B is an end view of the embodiment shown in FIG. 2A at the tip of the finished hollow instrument.

FIG. 2D is a partial side view of the embodiments shown in FIGS. 2A-2C while being deformed. The hollow instrument having multiple bindings though each of the longitudinal spacing to join the fingers thereby reducing flexibility caused by localized buckling of the hollow instrument during deformation. It is believed that while in the root canal during a similar buckling of the lower finger, this reduced flexibility may cause the lower finger to deform inward towards the tube axis (e.g., file axis) thereby reducing cutting pressure locally or reducing finger contact with the root canal surface relative to a similarly shaped sold file.

FIG. 2E is a partial zoomed-in side view of the embodiment shown in FIGS. 2A-2C while being differently deformed showing minimal deformation of a finger along one side of the hollow instrument relative to localized buckling of another finger along an opposing side of the hollow instrument.

FIG. 3B is a zoomed-in top view of the embodiment shown in FIG. 3A. The finished hollow instrument having multiple (e.g., three) finger endodontic instrument having a single weld, which may enable one or more fingers (e.g., preferable each finger) to act independently of the other(s) and generally provides the maximum flexibility. The individual fingers with a small cross section are generally free to buckle individually (though not required) when placed in a tightly curved canal.

FIG. 3C is a side view of the embodiments shown in FIGS. 3A-3B being deformed. The hollow instrument having a single weld proximal to the tip shows increased flexibility caused by localized buckling of the hollow instrument during deformation. It is believed that while in the root canal during a similar deformation of the upper finger, this increased flexibility may cause the upper finger to deform thereby adding cutting pressure locally to the surface proximate to the deformed upper finger relative to a similarly shaped sold file.

DETAILED DESCRIPTION OF INVENTION

Figure 1A:
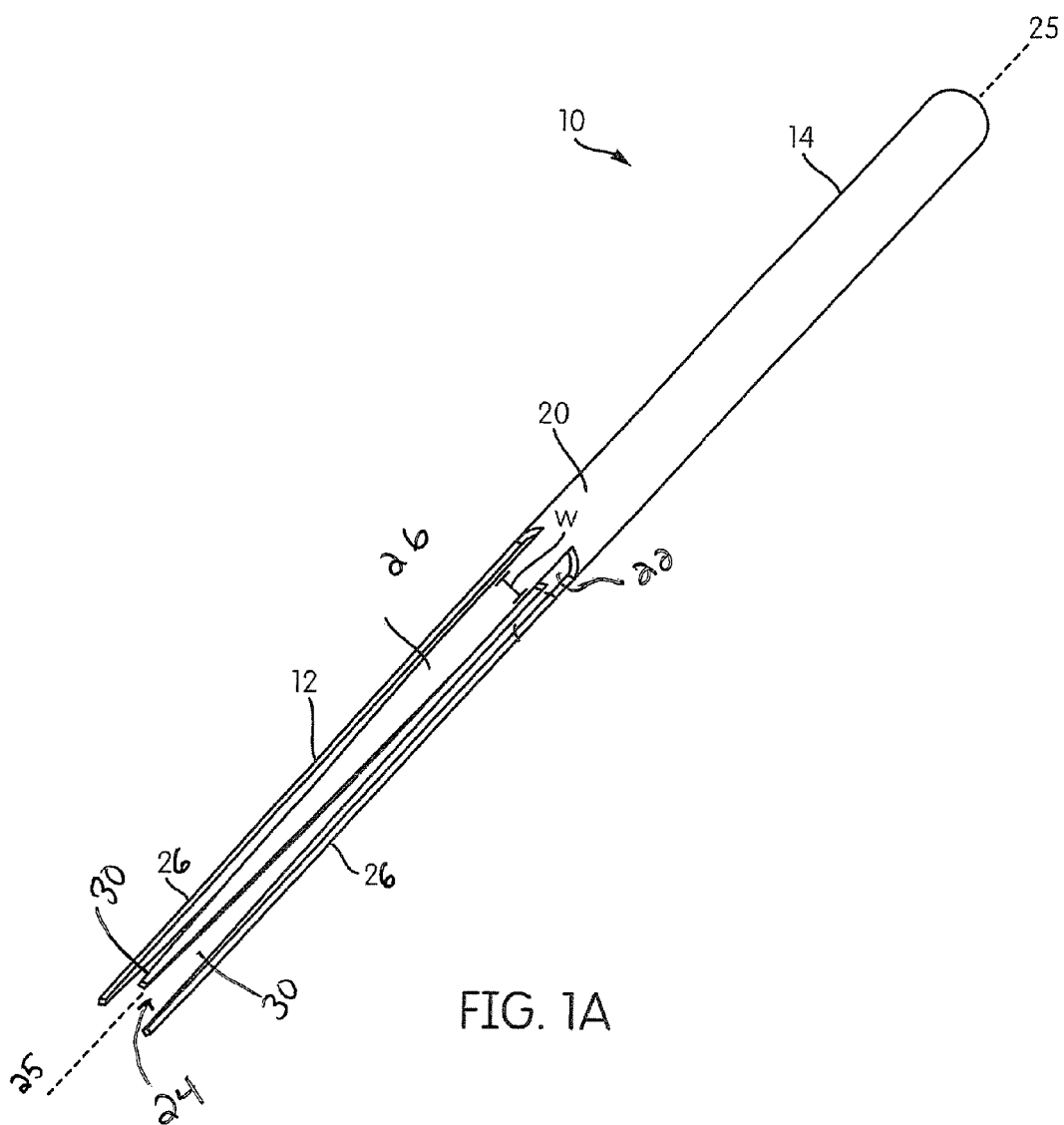
FIG. 1A, is a perspective view of one embodiment of the present invention that includes a semi-finished hollow instrument (e.g., after the cutting step). The semi finished hollow instrument having a plurality of fingers (e.g., three fingers), which have been designed to allow the desired geometry in the finished shape (prior to the deforming step). The shapes shown can be made using EDM, laser cutting, or conventional grinding.
Figure 1B:
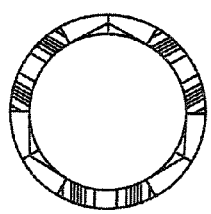
FIG. 1B is an end view of the embodiment of FIG. 1 at the tip of the semi-finished hollow instrument.
Figure 1C:
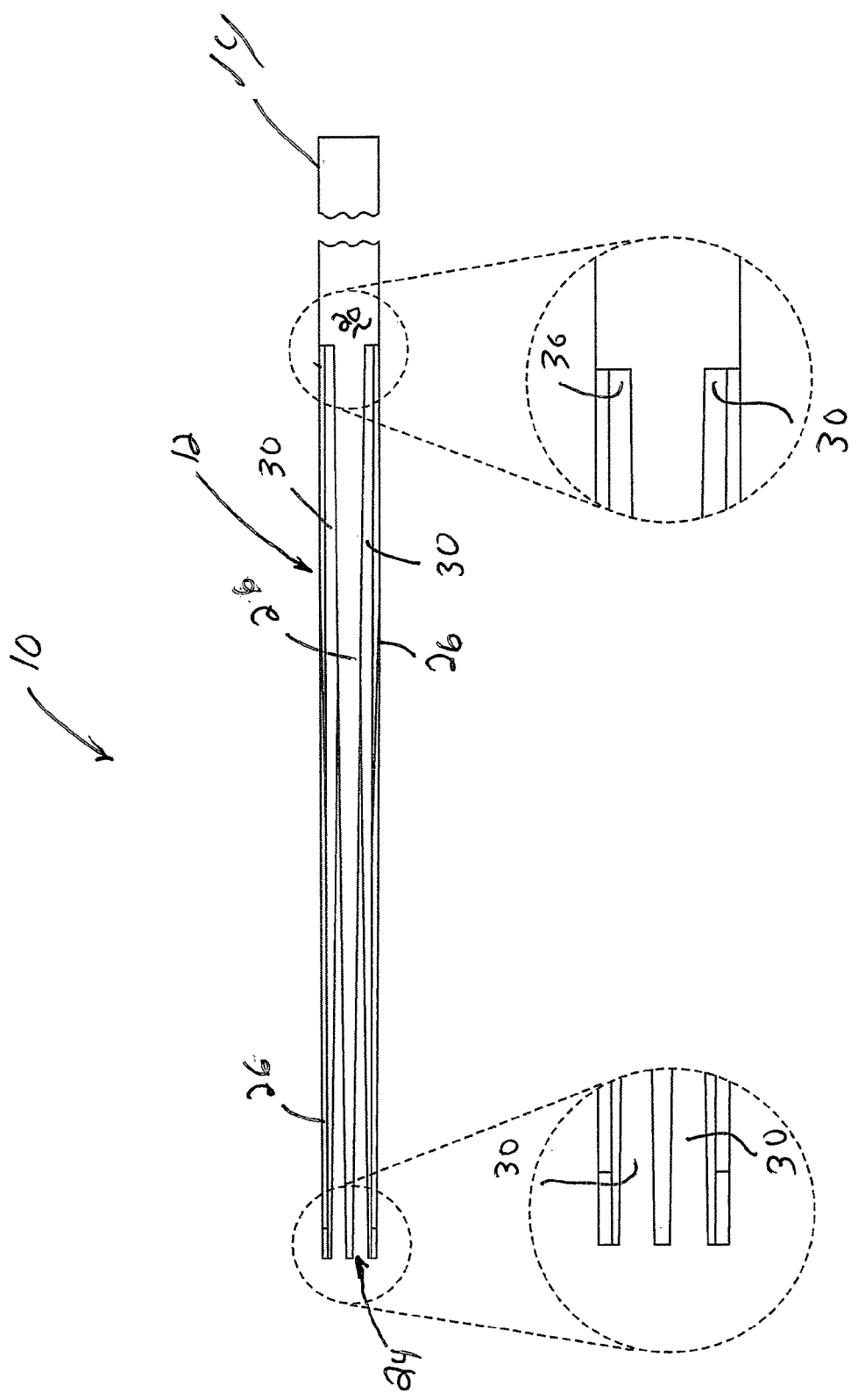
FIG. 1C is a top view of the embodiment shown in FIG. 1 showing end portions of the fingers that are angled from the exterior surface towards the interior surface such that the thickness at the end portion decreases towards the end of the semi-finished hollow instrument (e.g., tip portion) and showing the transition of the proximal end to the shaft portion where the fingers and longitudinal spacings of the shaft extend from the proximal end.

This invention relates to dental instruments in general. Specifically, this invention relates to endodontic hollow instruments for use in root canal cleaning and shaping procedures. In general, the channels to be widened and/or cleaned and/or shaped by the hollow instruments of the present invention are relatively long and narrow. The hollow instruments can be inserted completely to the end of a root channel or only partially into the channel, in which case only part of the channel will be widened and/or shaped and/or cleaned. As an illustrative, but non-imitative, example of the instrument of the invention embodiments' of an endodontic file for performing root canal treatments will be described hereinbelow.

The present invention provides an innovation of endodontic instrument that may be made of shape memory alloys (SMA) such as Nickel-Titanium (NiTi) based systems, Cu based systems Fe based systems, or any combination thereof (e.g., materials selected from a group consisting of near-equiatomic Ni—Ti, Ni—Ti—Nb alloys, Ni—Ti—Fe alloys, Ni—Ti—Cu alloys, beta-phase titanium and combinations thereof), non-shape memory alloys (e.g., stainless steel or otherwise, plastics, composites, or any combination thereof.

The present invention employs methods for manufacturing endodontic instruments (e.g., rotary files) from a sheet of material or a hollow member such as a tube. The sheet of material and/or the hollow member may be formed of Nitinol, stainless steel, other raw materials or combinations thereof. Advantageously, in one embodiment, the amount of material removed during the manufacturing process may be reduced by starting with a hollow shaped member (e.g., tubular shaped), optionally formed of Nitinol. The hollow shaped member may be generally close to the final desired shape of the endodontic instrument, thereby reducing the amount of material that needs to be removed (e.g., from grinding or otherwise process(es)). The hollow members are generally readily available in various lengths so as to enable mass production. In another embodiment, the sheet of material may be chemically milled to include a desired pattern of throughholes. The sheet material having the desired pattern may be subsequently rolled to form the hollow instrument (e.g., hollow endodontic file).

The preferred embodiment of the endodontic instrument of the invention, known herein as a hollow instrument (e.g., hollow file) that may be a rotary or reciprocating instrument. While current leading rotary files may be limited to constant tapered diameters, the hollow file may be used as instrument capable of a variable taper. When inserted into a narrow canal, the instrument may compress allowing it reduced contact with the walls of the canal in each radial plane along a portion of the longitudinal axis of the canal thereby minimizing (e.g., reducing) canal wall removal relative to a file with a generally constant taper. Alternatively, or in addition to, the instrument may expand when inserted into the narrow canal allowing it to adapt itself to the cross-sectional shape of the walls of the canal in each radial plane along a portion of the longitudinal axis of the canal so that contact with the canal wall is increased thereby maximizing (e.g., increasing) canal wall removal relative to a file with a generally constant taper. It is appreciated that one or more portions of the hollow instrument may be configured to compress in the radial plane along the shaft while one or more different portions of the hollow instrument may be configured to expand in the radial plane along the shaft. Finishing the hollow instrument by any of several surface modifications (such as diamond coating, vapor deposition, bead blast or otherwise) to have an improved cutting surface or edge.

Rotating and/or reciprocating rotationally and/or axially in the canal the hollow instrument removes tissue and debris from the canal and the canal wall. Desirably, the hollow center void of the hollow instrument may provide a conduit for debris as it is removed from the canal wall. Furthermore, it is contemplated that the hollow center void of the hollow instrument may be configured as a conduit for providing a solution to the root canal such as for irrigation to aid in cleaning process of the root canal. For example, material scraped from the wall of the canal passes may pass through the spacings between the fingers of the shaft portion into the hollow void from which it can easily be removed by rinsing or suction without stopping rotation and/or reciprocation of the instrument or withdrawing it from the root canal. In other embodiments, the debris can also be removed via the openings with the matrix of the shaft portion or by the space between the canal wall and the instrument. The design discussed herein may allow for fluids, such as antiseptic or saline solution, to continuously flow into the root canal, either through the center of the hollow instrument or between the outer surface of the hollow instrument and the canal wall, while the instrument is working, thus saving valuable time and improving the debridement and disinfection procedures. The constant flow also increases the efficiency of filing and prevents clogging the canal with dentin-mud and debris. Another advantage of the hollow instruments is that, in the extreme case of instrument failure and breakage inside the canal, the separated part of the instrument of the invention can be easily and safely removed, using specially designed extractors, no matter what the position of the broken piece of the instrument in the root canal.

After part of the crown is removed and the pulp is cleaned out of the pulp chamber, and a sufficient access to the canal is obtained, the hollow instrument is inserted into the root canal. As the hollow instrument is pushed into the canal, its increased flexibility allows it to be guided to the apical end of the root canal by following the path of least resistance (through the pulp rather than the much harder dentine). Prior art files can also adapt themselves to the canal shape longitudinally but are unable to change their volume and contour as can the hollow instrument of the present invention. Additionally the solid structure of the prior art files makes them less flexible than the hollow shaped instrument designs described herein.

A first embodiment of the present invention includes a hollow instrument 10 having an elongated shaft portion 12 with a proximal end 14 to which may be secured to an attachment end 16 for attachment to a handpiece (e.g., a rotary device). The shaft portion 12 (e.g., working portion) is configured to be inserted into and removed from the root canal of the tooth and includes a tip 114.

The hollow instrument 10 may be provided in various sizes having any width, length, and/or thickness sufficient for accommodating a dental handpiece and/or removing debris according to the present invention. It is appreciated that the hollow instruments described herein may be formed having different lengths and/or various file tapers. For example, it is appreciated that the diameter may be reduced so that the shaft portion 12 includes greater than about 0% taper, preferably from about 1% to about 10% taper, and most preferably from about 2% to about 6% taper.

The semi-finished hollow instrument 10 may further include a exterior surface 20 and an interior surface 22 defining a hollow center void 24 at least partially bounded by a plurality of fingers 26. The fingers 26 generally extend from the proximal end 14 to define the shaft portion 12 and may be interconnected in the finished hollow instrument by at least one binding. Examples of the binding may include, but is not limited to, welding (e.g., arc, ultrasonic, laser, resistance, extrusion, induction, vibration, spin, dielectric, microwave, or otherwise), soldering, brazing, frame joints, adhesive, cement, mechanical fasteners, (e.g., nails screws, bolts, rivets, or otherwise) and otherwise or combinations thereof. Each finger may include a pair of opposing side walls 28 defining a finger width W therebetween and extend between the exterior surface 20 and the interior surface 22 to define a finger thickness. The side walls 28 may form an edge, may be curved, flat, angled, or otherwise while extending from the proximal end 14, between the surfaces 20,22, or a combination of both.

Preferably, the hollow void 20 may completely extend through the proximal end 14 (in addition to the shaft portion 12) generally longitudinally along the tube axis (e.g., file axis) 25 thereby providing a longitudinal throughhole, though not required. Alternatively, the hollow void may not extend through the proximal end such that the proximal end is not hollow (e.g., solid) or the hollow void may only partially extend through the proximal end generally longitudinally along the file axis 24.

Figure 9:
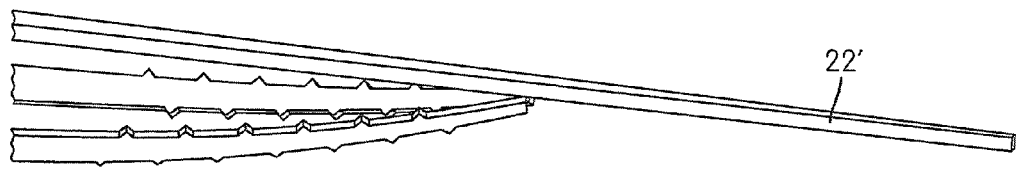
FIG. 9 is a partial perspective view of another embodiment of the present invention resulting from the semi-finished hollow instrument shown in FIG. 1A. This embodiment includes one finger that is longer than and extends past the others fingers. The other (e.g., shorter) fingers may be joined to the longer finger by a least one binding at a distance from the tip. This may allow even more flexibility at the tip and the hollow instrument overall.
Figure 10:
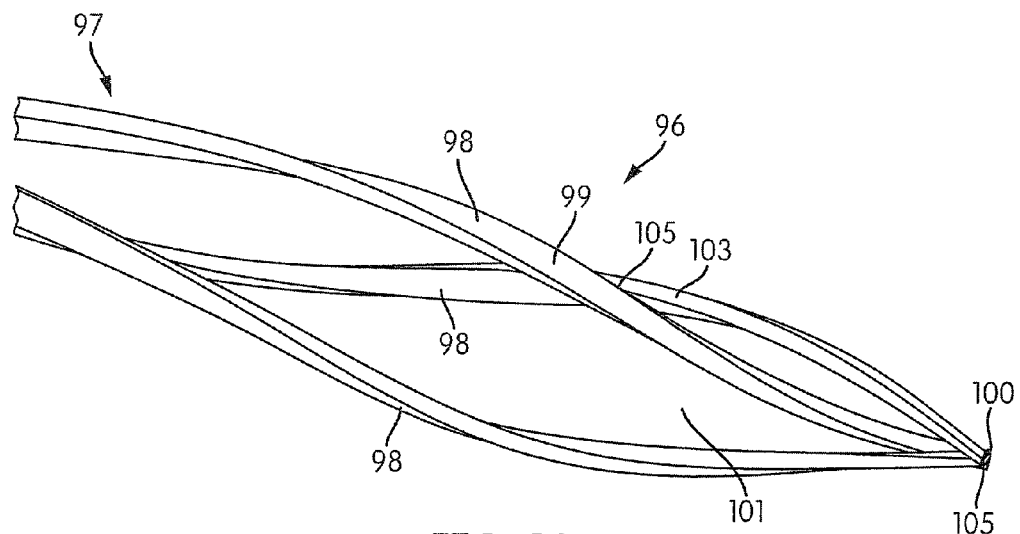
FIG. 10 is a partial perspective view of another embodiment of the present invention resulting from the semi-finished hollow instrument shown in FIG. 1A. This embodiment includes helical cut fingers in the hollow instrument. The helical cut fingers may be joined by at least one binding at the tip alone (as shown) or by multiple binding along one or more portions of the longitudinal openings between adjacent fingers. The helical cut fingers may provide more flexibility along each helix. Optionally, sharp edges could be added (as shown previously) for more aggressive cutting.

The semi-finished hollow instrument 10 may further include one or more spacings 30 extending between adjacent fingers 22 and from the proximal end 14 to the tip 114. As shown in FIG. 1A, as the finger widths (e.g., distance between side walls 28) decreases towards the tip 18, the width of the spacing between adjacent fingers increases towards the tip 114. However, it is appreciated that the fingers 22 may be formed of any shape or size and may be the same or different. For example as shown in FIG. 9, finger 22' is generally longer any may include a different (e.g., smaller) cross-section than the remaining fingers 22.

Figure 5:
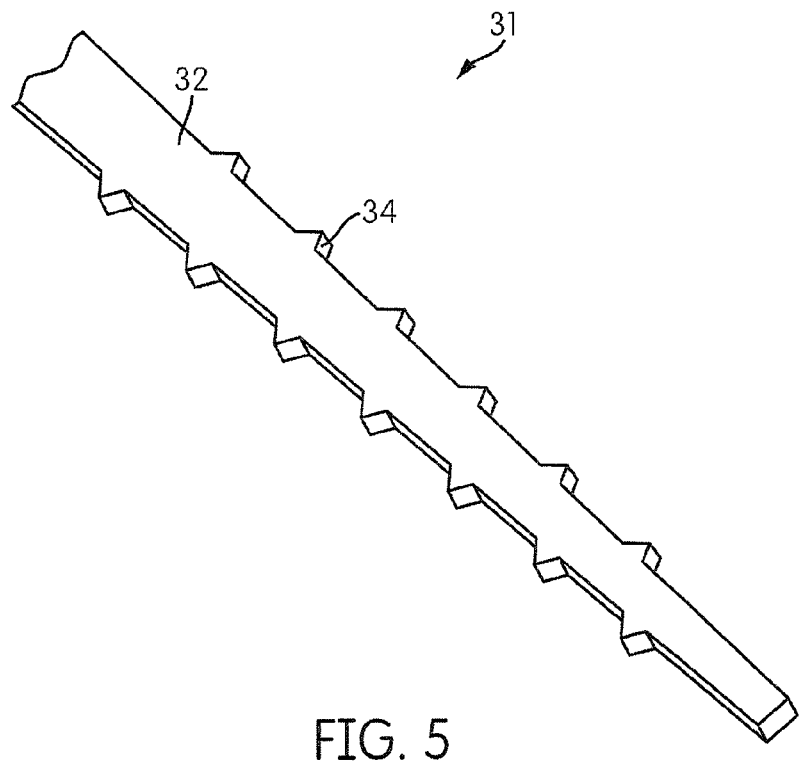
FIG. 5 is a partial perspective view of another embodiment of a finger shown in FIG. 1A having multiple boss portions such as "teeth" (e.g., sharpened teeth) extending from the opposing side walls of the finger. Advantageously, cutting efficiency may be increased utilizing the one or more boss portions.
Figure 6:
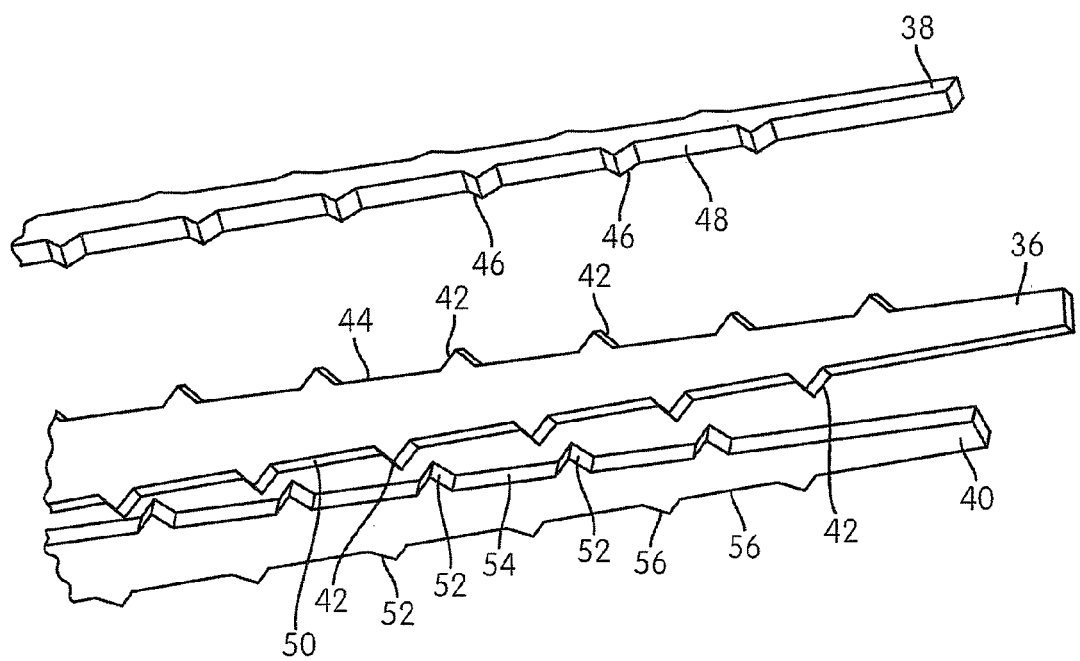
FIG. 6 is a partial perspective view of another embodiment of the semi-finished hollow instrument shown in FIG. 1A having multiple boss portions such as "teeth" (e.g., sharpened teeth) extending from the opposing side walls of each finger. It is appreciated that during the forming step, the boss portions having sharp corners are cut out from the fingers while maintaining the integrity of the hollow instrument generally intact. The corners may be generally spaced so that a clearance may be provided relative to one another when another finger may be compressed.
Figure 7:
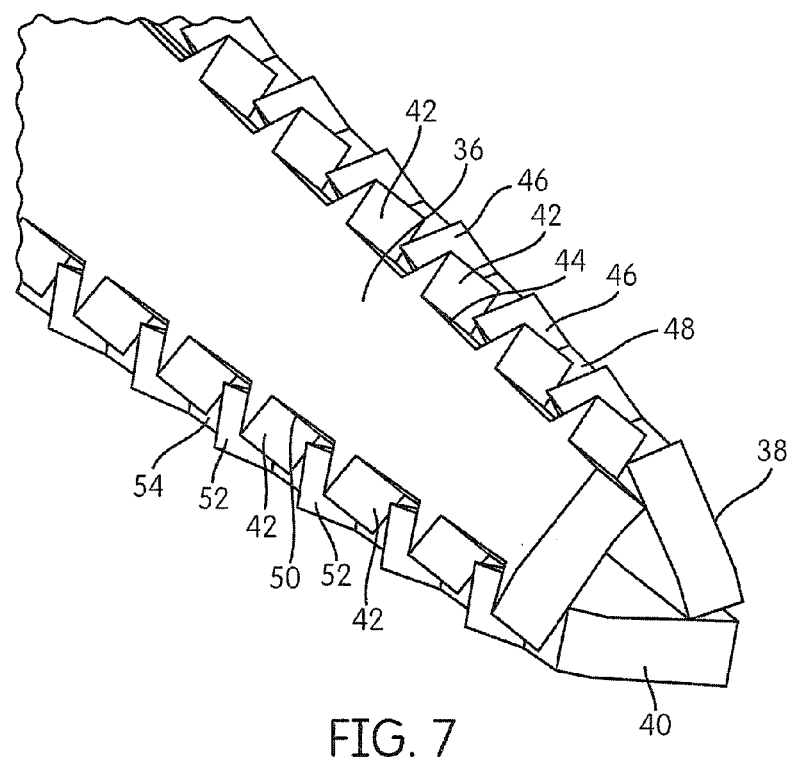
FIG. 7 is a partial perspective view of another embodiment of the present invention that resulting from the semi-finished hollow instrument shown in FIG. 1A showing the individual fingers having the boss portions collapsed. The boss potions being in a staggered relationship such that the sharp corner of one boss portion along one finger merges generally between two boss portions of an adjacent finger to provide a series of cutting edges. The fingers may be welded into this geometry creating a multi-sided, sharp, tapered hollow instrument.

In another embodiment, the semi-finished hollow instrument 10 may include one or more fingers 32 having boss portions 34 extending from at least one side wall 28 (e.g., such as in a saw tooth arrangement). The boss portions may be configured for aiding in the removal of debris (e.g., enhanced cutting). In one specific example as shown in FIGS. 5-7, the hollow instrument includes a first finger 36, a second finger 38, and a third finger 40 with each finger having multiple boss portions extending outward (e.g., generally transversely from the fingers) from both opposing side walls 28. In this specific example, the boss portions may be positioned in a staggered relationship such that they are generally similarly spaced along each opposing wall 28, while being offset from one opposing wall relative to the other opposing wall. As shown in FIG. 7, this staggered relationship allows for one boss portion of one finger to be positioned between two boss portions of an adjacent finger. More particularly the boss portions 42 along the first opposing wall 44 of the first finger 36 are positioned respectively between the boss portions 46 along the second opposing wall 48 of the second finger 38 and the boss portions 42 along the second opposing wall 50 of the first finger 36 are positioned respectively between the boss portions 52 along the first opposing wall 54 of the third finger 40 while the boss portions 52 along the second opposing wall 56 of the third finger 40 are positioned respectively between the boss portions 46 along the first opposing wall 58 of the second finger 38.

It is appreciated that the respective boss portions may have a shape and/or size that is the same or different along one or both opposing walls of each finger or from one finger to another. Preferably the boss portions may be shaped to include an angle have a point such as a triangle, though others shapes are contemplated (e.g., curved such as ovals, circles, squares, rectangles, or otherwise).

Figure 8:
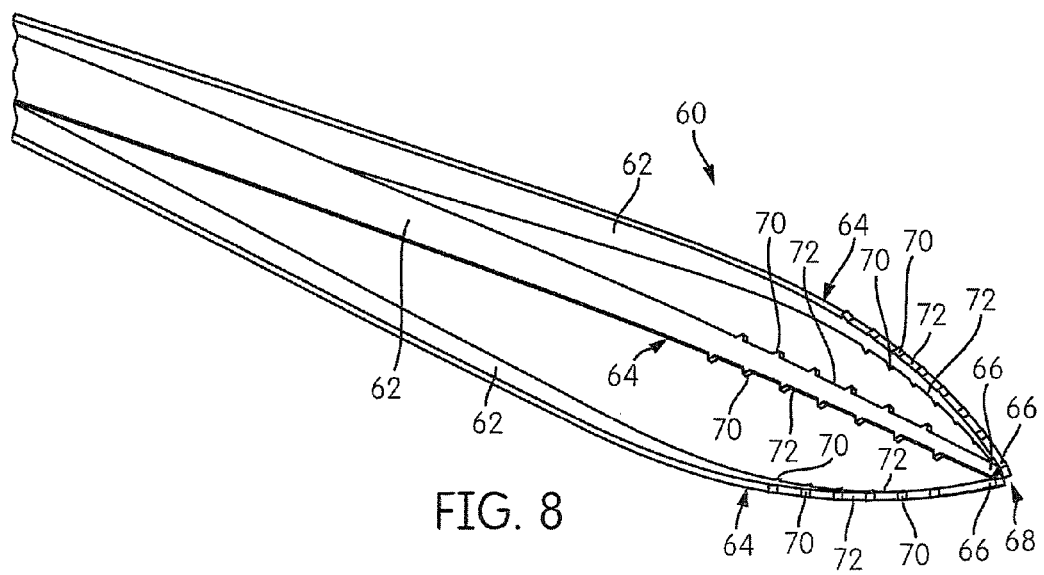
FIG. 8 is a partial perspective view of another embodiment of the present invention resulting from the semi-finished hollow instrument shown in FIG. 1A. This embodiment includes a non-uniformly tapered hollow instrument having boss potions on each finger only along portions of the shat near the tip. By shaping or curving the fingers (e.g., pre-bent or pre-curved) prior to joining step the fingers may provide more radial force thereby cutting even more aggressively. Optionally, the sharp edges may extend the length of the fingers or be localized at any location along the one or more fingers to provide additional cutting at various points along the endodontic hollow instrument (e.g., file). Therefore, the endodontic hollow instrument could provide more aggressive cutting apically or coronally.

In another embodiment, the hollow instrument may include a variable taper defined by one or more pre-bent fingers having at least one curve or bend (e.g., convex curve, concave curve or a combination of both). In one specific example as shown in FIG. 8, a hollow instrument 60 includes a plurality of pre-bent fingers 62, each having a concaved curve 64. The pre-bent fingers 62 extend longitudinally from the proximal end 14 while being increasingly displaced from the file axis 25 so that the instrument cross-section (e.g., diameter) may be increased. The ends 66 of the pre-bent fingers 62 may be displaced towards the file axis 25 (e.g., decreasing the instrument cross-section) thereby forming the tip 68 of the hollow instrument 60. Preferably, the tip 68 may be positioned along the file axis 25, though not required. It is appreciated that one or more of the fingers 62 may further include boss portions 70 (e.g., protrusions) along the entire finger or along one or more portions thereof. In one specific example as shown in FIG. 8, each finger includes a plurality of boss portions 70 along a portion of the opposing walls 72 that extends between the curve 64 (e.g., the apex of the curve or offset portion) and the end portion 66 of fingers 62.

Figure 4:
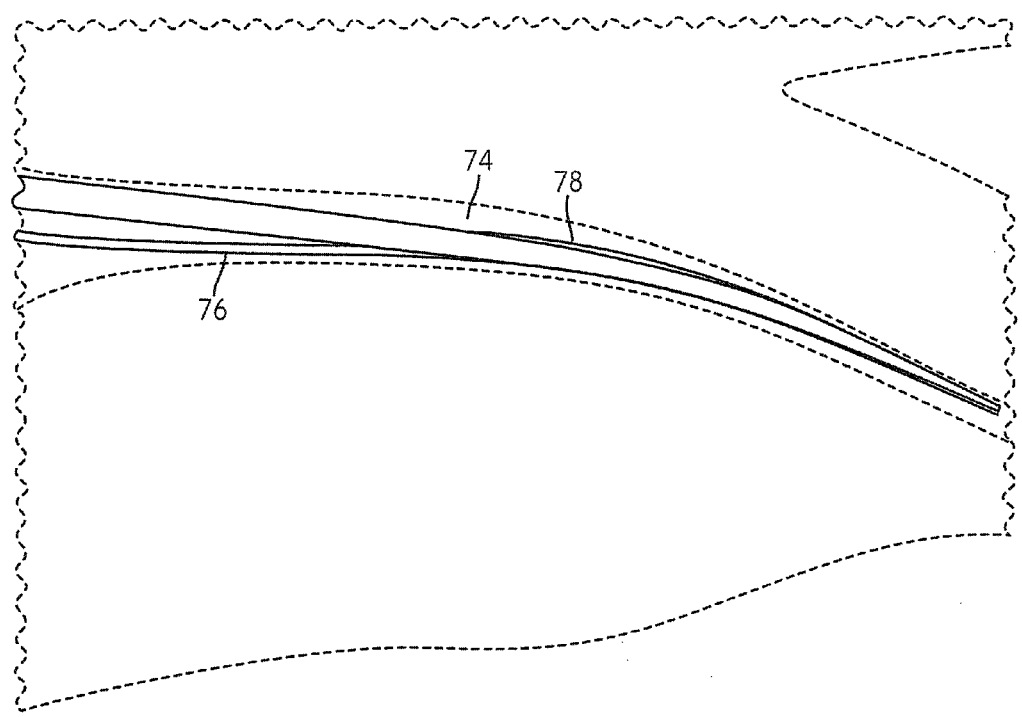
FIG. 4 is a side view of a root canal and the embodiment with single bindings shown in FIG. 3A showing the hollow instrument taking on a generally S-shaped configuration in a canal as each finger acts independently near the end of the longitudinal openings towards the proximal end of the hollow instrument. The lower finger is generally free to adapt to the shape of the canal thereby expanding (e.g., deforming outward near the proximal end) and compressing (e.g., deforming inward near the middle portion of the shaft) along different portions of the lower finger.

Advantageously, instrument compression and/or expansion during removal of debris (e.g., material) may be increased in a hollow instrument having a pre-bent configuration such as the hollow instrument 60. For example, it is appreciated that during the removal of the infected area of the root canal 74 and surrounding area (FIG. 4), the hollow instrument may typically encounter some resistance as portions of the fingers contact the material to be removed (e.g., dentin, pulp, nerve tissue and/or infected material) within the tooth. This instrument resistance and optionally any downward force by the operator towards the apex of the root canal during use of the hollow instrument, may cause the finger portions to expand (e.g., generally increase finger displacement from the file axis), collapse (e.g., generally decrease finger displacement from the file axis), or a combination of both. Expansion and/or collapsing of one or more portions of the fingers generally may occur in the transverse (e.g., radial) direction, the longitudinal direction, or a combination of both relative to the file axis so that surface contact with the root canal (e.g., the material to be removed) may be increased. More particularly, as the instrument resistance occurs (e.g., contacting the dentin and/or root canal wall) one or more portions of the fingers may be deformed along a path of least resistance (e.g., towards the pulp material) so that dentin removal may be minimized while maximizing contact with the pulp material thereby maximizing pulp material removal.

Figure 2C:
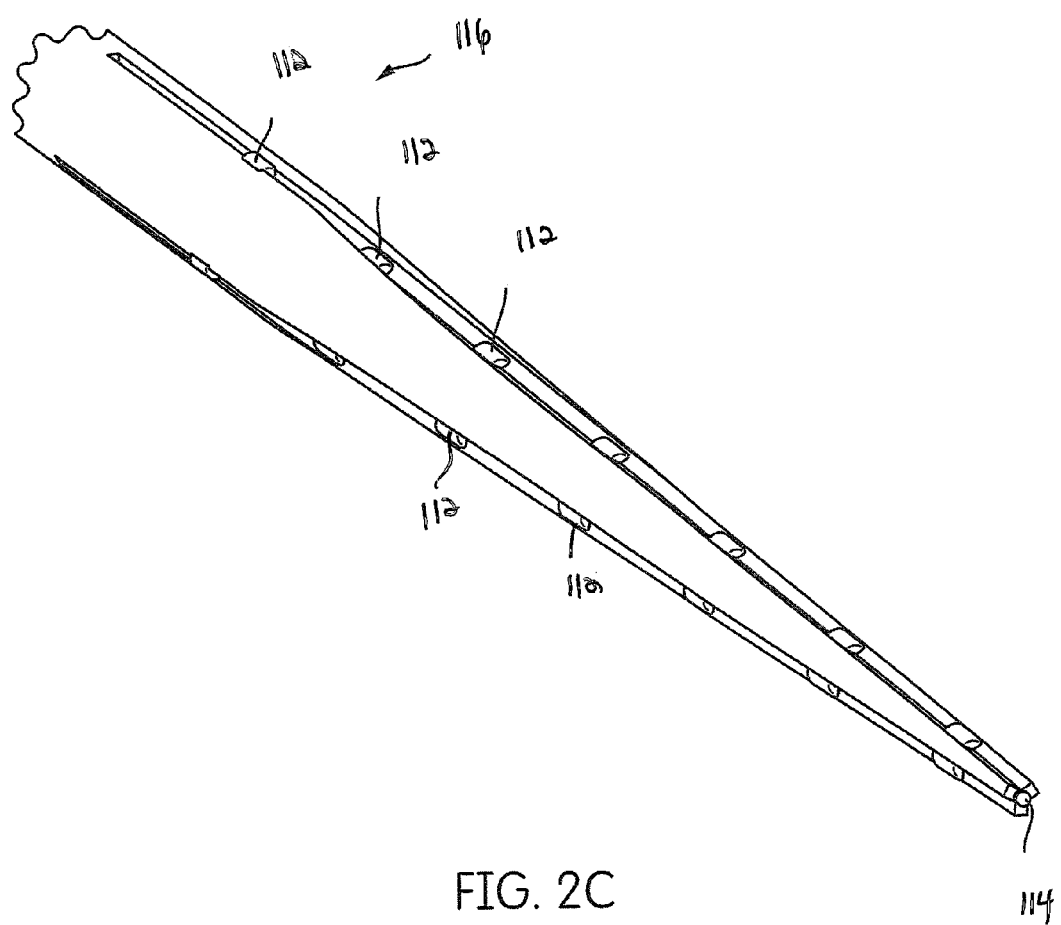
FIG. 2C is a zoomed-in perspective view of the embodiment shown in FIG. 3 showing the multiple bindings spacedly positioned through each of the longitudinal openings between each of the fingers.

FIGS. 2D-2E show the hollow instrument 116 that has been deflected (e.g., bent) upon contact with a surface 76. The hollow instrument 116 includes a plurality of fingers being interconnected by a plurality of bindings 112. The plurality of fingers and selective placement of the bindings 112 cooperate to allow for increased deflection of the hollow instrument 116. For example, as the shaft portion 80 is deflected downward, the plurality of fingers may be compressed (e.g., decrease in the instrument cross-section relative to the instrument cross-section in a non-deflected state) such that a first finger 82 is displaced towards the other fingers 84 thereby allowing improved flexibility of the hollow instrument 116. In doing so, the hollow instrument 116 may be further deflected (e.g., bent) to increase adaptation of hollow instrument to the cross-section of the root canal relative to a similarly formed solid instrument. By increasing flexibility (e.g., adaptation to the root canal), the hollow instrument may be configured to increase removal of pulp material while decreasing removal of dentin material. It is appreciated that the deflection of the shaft portion 80 is for illustration purposes only and similar instrument compression results may occur upon deflection of the shaft portion 80 in other directions.

It is appreciated that the hollow instruments described herein may not require binding to maintain the hollow instrument in its desired shape. This may be dependent on the deformation or thermal shape setting necessary to maintain the desired geometry.

Figure 3A:
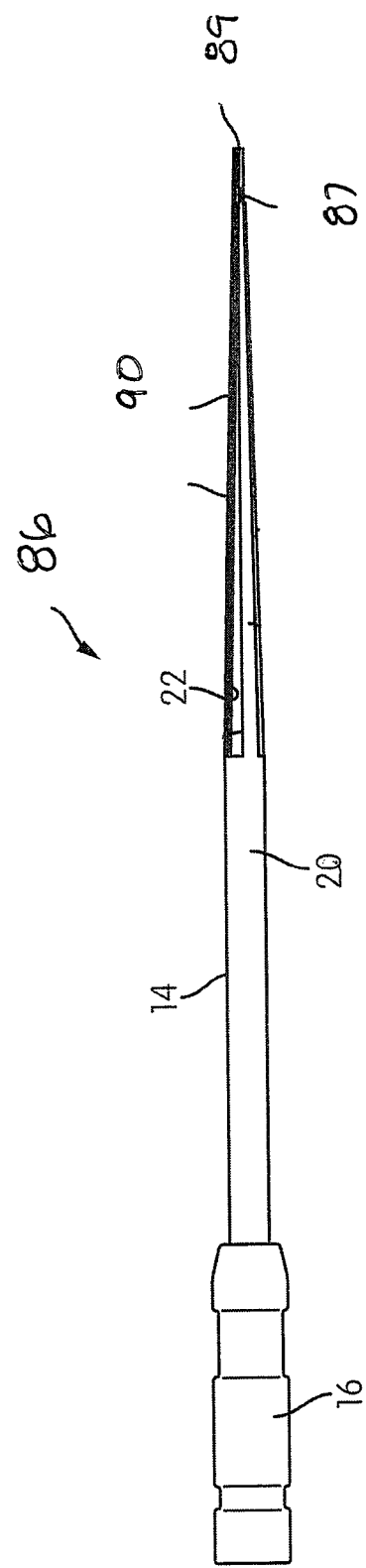
FIG. 3A is a top view of another embodiment of the present invention resulting from the semi-finished hollow instrument shown in FIGS. 1A-1C. This embodiment is similar to the embodiment shown in FIG. 2 but for the plurality of tapered fingers (e.g., three fingers) being interconnected at a tip portion by a single weld across each longitudinal spacing to adjacent fingers (e.g., for this specific example, three total weld, one between each of the three fingers through each of the three longitudinal spacings).

Furthermore, FIG. 3C show the hollow instrument 86 that has been deflected (e.g., bent) upon contact with a surface 88. The hollow instrument 86 includes a plurality of fingers being interconnected by at least one binding 87 (though not required) proximate to the tip 89. The plurality of fingers and selective placement of the binding 87 cooperate to allow for increased deflection of the hollow instrument 86. For example, as the shaft portion 90 is deflected upward, the plurality of fingers may be expanded (e.g., increase in the instrument cross-section relative to the instrument cross-section in a non-deflected state) such that a first finger 92 may be displaced outwards away from the other fingers 94 thereby allowing improved flexibility of the hollow instrument 86. In doing so, the hollow instrument 86 may be further deflected (e.g., bent) to increase contact of hollow instrument to the surface of the root canal relative to a similarly formed solid instrument. By increasing flexibility and allowing for instrument expansion, the hollow instrument 86 may be configured to increase surface contact of the root canal wall thereby increasing removal of material. It is appreciated that the deflection of the shaft portion 90 is for illustration purposes only and similar instrument expansion results may occur upon deflection of the shaft portion 90 in other directions.

In another embodiment, the present invention may include a hollow instrument 96 having a shaft portion 97 including a plurality of twisted fingers 98 that define a hollow void 99 therebetween. The fingers 98 being interconnected by at least one binding proximate to the tip 100. Optionally, the fingers 98 may include a first finger 99 that extend through the hollow void 101 to an opposing side of the shaft portion 97 thereby contacting at least one different finger 103. When included, the plurality of fingers 98 may be interconnected by a plurality of bindings 105.

The twisted fingers 98 extend longitudinally from the proximal end 14 while being increasingly displaced from the file axis 25 so that the instrument cross-section (e.g., diameter) may be increased. As the fingers 98 extend from the proximal end 14, each finger may be rotated thereby forming a spiral (e.g., a helical having clockwise and/or counter clockwise rotations). It is appreciated that each finger 98 may form at least one spiral having a rotation of at least one at least about 5 degrees, preferably at least about 30 degrees, and more preferably at least about 90 degrees. Furthermore, each finger may form at least one spiral having a rotation of less than about 360 degrees, preferably less than about 315 degrees, and more preferably less than about 270 degrees. For example, each finger may form at least one spiral having a rotation ranging from about 5 to about 360 degrees, preferably from about 30 to about 315 degrees, and more preferably from about 90 to about 270 degrees. Desirably each finger includes a plurality of spirals.

Figure 11:
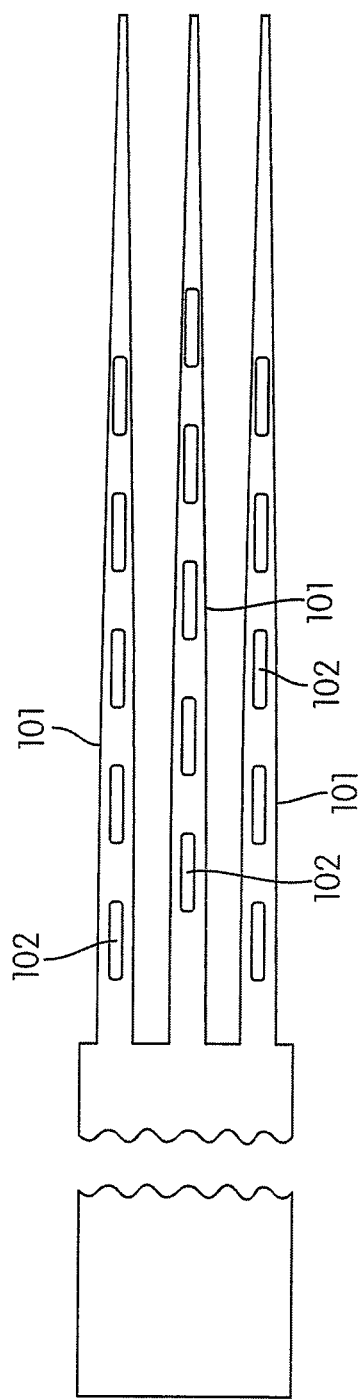
FIG. 11 is a partial top view of another embodiment of a semi-finished hollow instrument in an unrolled orientation having multiple spaced openings extending transversely (e.g., radially) through each tapered finger. The multiple spaced openings of one finger being positioned in a staggered relationship relative to the adjacent fingers.
Figure 12:
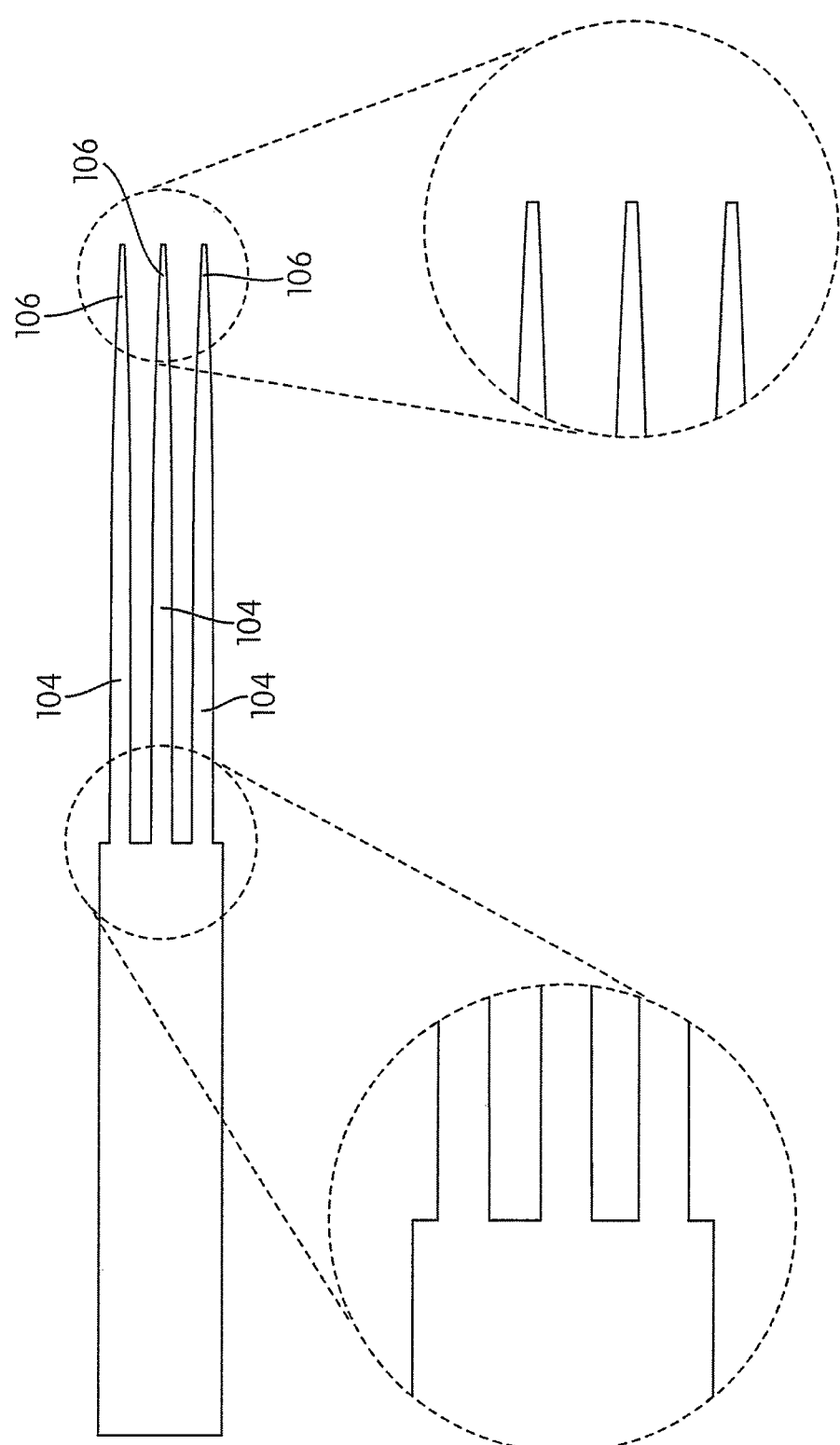
FIG. 12 is a top view of the semi-finished hollow instrument shown in FIG. 1A in unrolled orientation having tapered fingers that decrease towards the tip and tapered longitudinal openings that increase towards the tip.

It is appreciated that the hollow instruments discussed herein may further include or alternatively include one or more of the following features: a tapered fingers 101 including one or more openings 102 extending from the exterior surface to the interior surface (FIG. 11); fingers having a body portion 104 with generally constant width and a tapered end portion 106 (FIG. 12); fingers interconnected by multiple bindings 108, the fingers defining a hollow void 108 extending through the tip 110 (FIG. 2B); fingers interconnected by multiple bindings 112 having an end binding 112 to define a bound tip 116 such that there is not a hollow void extending therethrough (FIG. 2A).

Figure 13A:
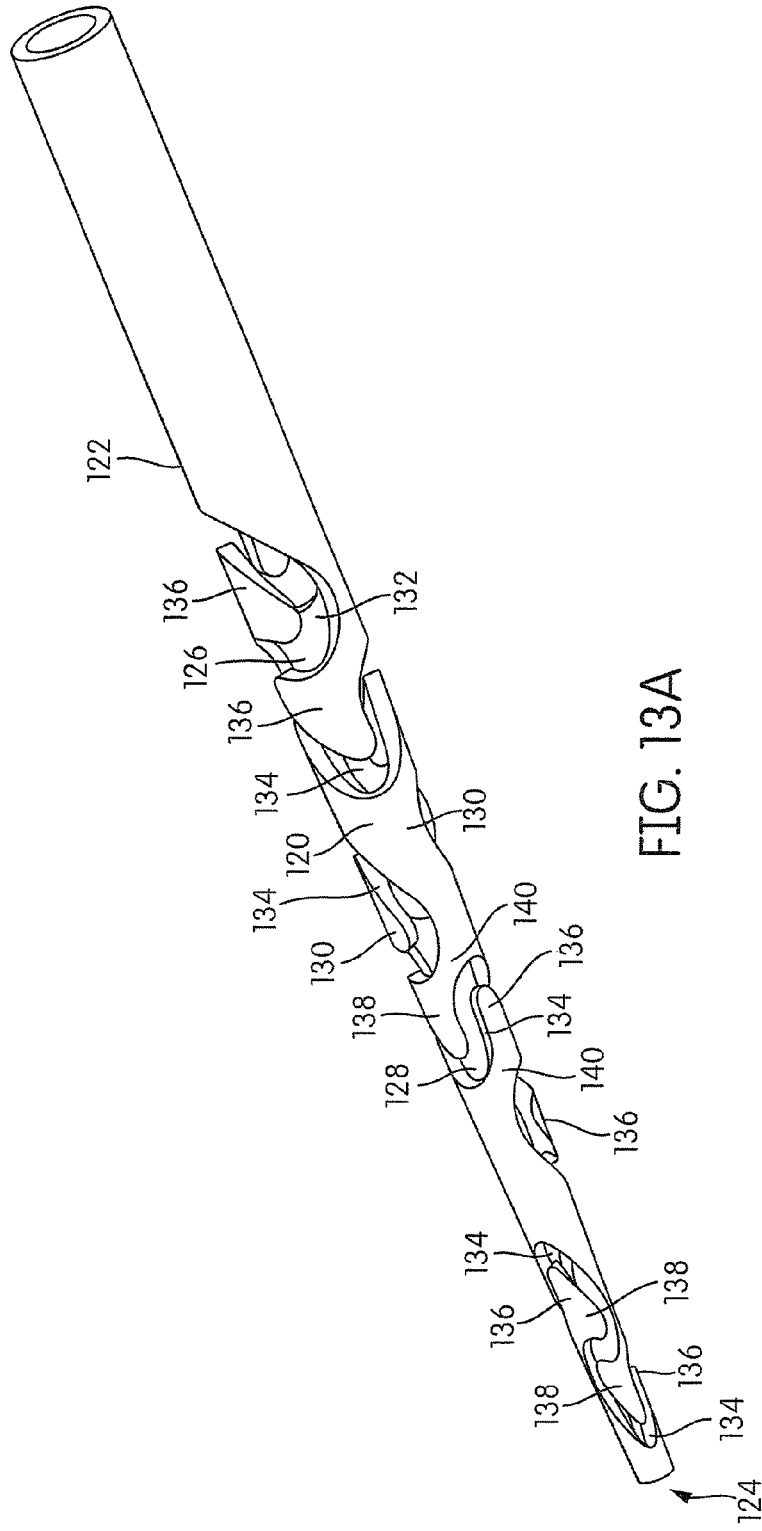
FIG. 13A is a perspective view of another embodiment of the present invention that includes a hollow instrument having a variable groove extending along the hollow instrument. The variable groove having a series of S-shaped curves that decrease in amplitude to accommodated the taper of the hollow instrument. In one specific embodiment, the variable groove may be cut into a tapered hollow tube.
Figure 13B:
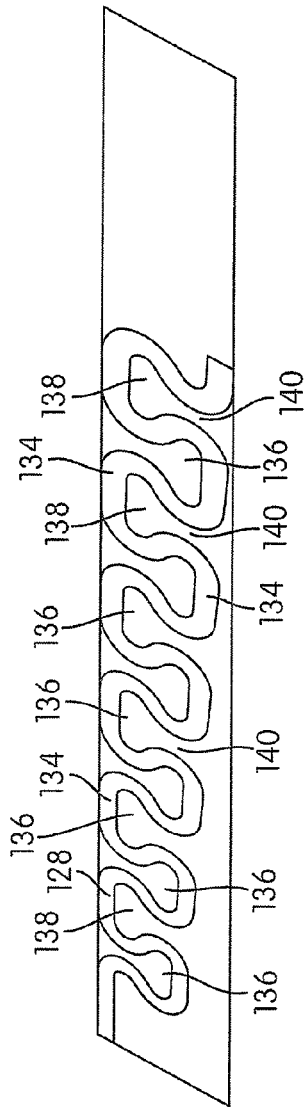
FIG. 13B is a top view of a sheet material having the variable groove cut therein to defines series of the S-shaped curves. The groove may be cut into the sheet material by lasers or otherwise or may be chemically milled (e.g., photochemically machined) to remove material. The sheet material may be formed (e.g., shaped) according to a desired geometry prior to being rolled for forming a taper hollow instrument.

In another embodiment, the present invention may include a hollow instrument 118 having an elongated shaft portion 120 with a proximal end 122 to which may be secured to an attachment end (or a handle) for attachment to a handpiece (e.g., a rotary device). The shaft portion 120 (e.g., working portion) may be configured to be inserted into and removed from the root canal of the tooth and includes a tip 124. The shaft portion 120 (and optionally the proximal end 122) defines a hollow void 126 extending therethrough to the tip 124. The hollow instrument 118 may further include at least one groove 128 extending longitudinally from the proximal end 122. The groove 128 further extends radially between an exterior surface 130 and an interior surface 132 and includes a width extending between opposing walls 134. The opposing walls 134 may be curved, flat, angled, or otherwise. The groove 128 may be in general communication with the hollow void 126. The groove 128 may be a continuous groove or part of multiple grooves and may be defined by various shapes and/or sizes. As shown in FIGS. 13A-13B, the groove 128 extends from the proximal end 122 to the tip 124 and includes a generally decreasing width towards the tip 124, however a constant width is also appreciated. The groove 128 may be include multiple curve portions 134 (e.g., S-shaped portions or otherwise) of decreasing amplitude to accommodate the taper of the hollow instrument 118. The curve portions 134 of the groove 128 generally define projections 136 formed by the opposing walls 134 and the exterior and interior surfaces 130,132. The projections 136 and the opposing walls 134 provide a cutting edge for removal of material. In one specific embodiment, the projections 136 may include a head portion 138 and a neck portion 140 (e.g., being integrally connected to the shaft portion 120), the head portion 138 having a width greater than the neck portion 140. It is appreciated that the head portion 138 may be a generally curved or arcuate shaped portion, though not required.

In another embodiment, the present invention may include a hollow instrument 142 having an elongated shaft portion 144 with a proximal end 146 to which may be secured to an attachment end (or a handle) for attachment to a handpiece (e.g., a rotary device). The shaft portion 144 (e.g., working portion) may be configured to be inserted into and removed from the root canal of the tooth and includes a tip 148. The shaft portion 144 (and optionally the proximal end 146) may define a hollow void 150 extending therethrough to the tip 148. The shaft portion 144 includes an exterior surface 152, an interior surface 154 that at least partially defines the hollow void 150, and a matrix 156 formed from a plurality of openings 158 extending at least partially through the shaft portion 144. Preferably, the matrix 156 includes a plurality of openings 158 that extend from the exterior surface 152 to the interior surface 154 thereby forming a throughhole in communication with the hollow void 150. The matrix 156 further includes channels 160 extending between the exterior and interior surfaces 152, 154 and the openings 158. The channels 160 may be flat, angled, curved, or otherwise and any combination thereof. The openings 158 may be formed in various shapes (e.g., squares, rectangles, diamonds, triangles, circles, other polygonal shapes, or otherwise shapes) and/or sizes. The matrix 156 may include openings 158 that are the same or different.

The present invention may further include a process of producing a hollow instrument (e.g., dental instrument such as an endodontic file). The method for forming the hollow instrument may include one or more of the following steps and combinations thereof: Providing a hollow tube (e.g., a medical tube such as a hypodermic needle tube) being dimensioned generally similar to the desired finished size of the hollow instrument. Cutting the tubing wall (e.g., using laser cutting or water jet cutting, or otherwise) following a predetermined pattern. Desirably, the predetermined pattern cut into the hollow tube may form at least one and preferably several abrasive cutting edges to achieve desired cutting properties. Deforming the hollow tube into a desired final shape. Joining (e.g., binding) portions of the cut pattern along the hollow tube to form the hollow instrument. Finishing the hollow instrument by any of several surface modifications (such as diamond coating, vapor deposition, bead blast or otherwise) to have an improved cutting surface or edge.

In a specific example, the present invention may provide for a method of manufacturing the endodontic instrument including one or more of the following steps and combinations thereof: 1) The rotary file is made using hollow tubing of the desired finished size. 2) The tubing wall is cut (using laser cutting or water jet cutting for example) following a pattern of the desired final shape. The pattern cut in the tube can create any of several abrasive cutting edges to achieve the desired cutting properties. 3) The tubing is deformed to the desired final shape. 4) The tubing is joined (by means of welding for example) at points along the cut pattern to form the desired final shape. 5) The finished part can then be altered by any of several surface modifications (such as diamond coating, vapor deposition, bead blast) to have an improved cutting surface or edge. An embodiment of the rotary file includes tapered cut longitudinal members which meet at the distal end to form a standard tip size and taper. Another embodiment would be a curved and circumferential pattern around the tube which would enable a final shape that has helical members. The resulting geometry eliminates the core of the rotary file and improves file flexibility and provides a void for movement of debris during root canal therapy.

As discussed herein, it is appreciated the joining step may be optional and that the deformation step alone may be sufficient to maintain the deformed tube in its desired shape. For example, by forming in the case of stainless steel or thermal shape setting by temperature in the case of a NiTi.

It is appreciated that the hollow tube may be provided as a solid object that may be bored out to form the hollow void therein. The hollow void may extend longitudinally through the entire length of the tube or may extend longitudinally through only a portion thereof (e.g., only through the portion that may become the shaft portion.

The present invention may further include another process of producing a hollow instrument (e.g., dental instrument such as an endodontic file). The method for forming the hollow instrument may include one or more of the following steps and combinations thereof: Providing a sheet of material (e.g., metal sheet, plastic sheet, or otherwise and combinations thereof). Chemically milling (e.g., photochemically machining or photo etching) the sheet to remove material following a predetermined pattern. Desirably, the predetermined pattern milled into the sheet may form at least one and preferably several abrasive cutting edges to achieve desired cutting properties. Rolling the patterned sheet into a desired tubular geometry to form a hollow tube. Joining (e.g., binding) portions of the hollow tube to secure the hollow tube into the desired tubular geometry thereby forming the hollow instrument. Finishing the hollow instrument by any of several surface modifications (such as diamond coating, vapor deposition, bead blast or otherwise) to have an improved cutting surface or edge.

Figure 14A:
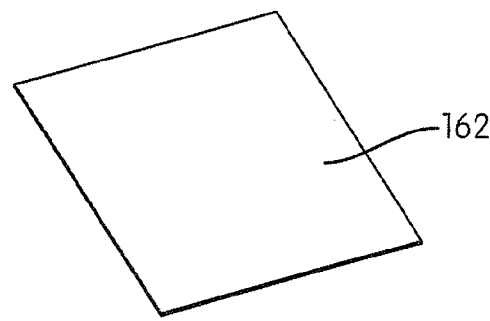
FIGS. 14A-14D are perspective top views of another embodiment of the present invention showing another process for forming a tapered hollow instrument. The process included providing a sheet of material (e.g., flat metal sheet). Photochemically machining the sheet material to have a desired pattern (e.g., geometry). The desired pattern being defined by multiple channels at least partially bounding multiple openings (e.g., diamond shaped openings). Stamping the sheet material having the desired pattern to a desired shape (e.g., tapered shape). Rolling the stamped sheet to a desired tubular shape. Joining the ends of the rolled sheet to secure the rolled sheet in the desired tubular shape to form the tapered hollow instrument. It is appreciated that the edges of the channels extending between an exterior surface and an interior surface may be configured for cutting.
Figure 14B:
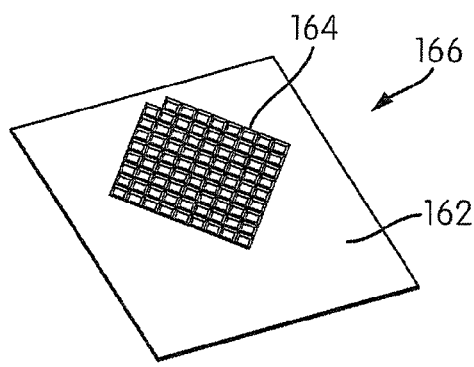
Figure 14C:
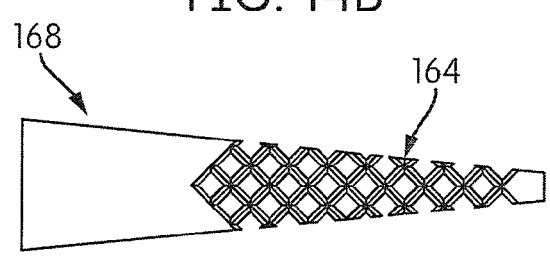
Figure 14D:
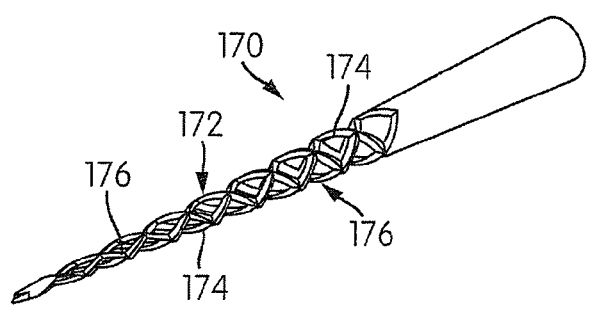

In one specific example, a sheet material 162 may be provided in a standard geometry (e.g., square, rectangular, or otherwise) as shown in FIG. 14A. A predetermined pattern 164 may thereafter be chemically milled into the standard geometry sheet 162 to form a patterned sheet 166 as shown in FIG. 14B. The patterned sheet may be shaped (e.g., by stamping, shape setting, or otherwise) into a desired geometry to form a shaped patterned sheet 168 as shown in FIG. 14C. The shaped patterned sheet 168 may be rolled into a desired tubular geometry to form a hollow tube (e.g., tapered hollow tube). The hollow tube may be joined (e.g., welded or otherwise) to secure the hollow tube into the desired tubular geometry thereby forming a hollow instrument 170 as shown in FIG. 14D. It is appreciated that the sheet material may be provided in a desired shaped geometry prior to the chemically milling step thereby possibly rendering the forming step thereafter unnecessary.

Figure 15A:
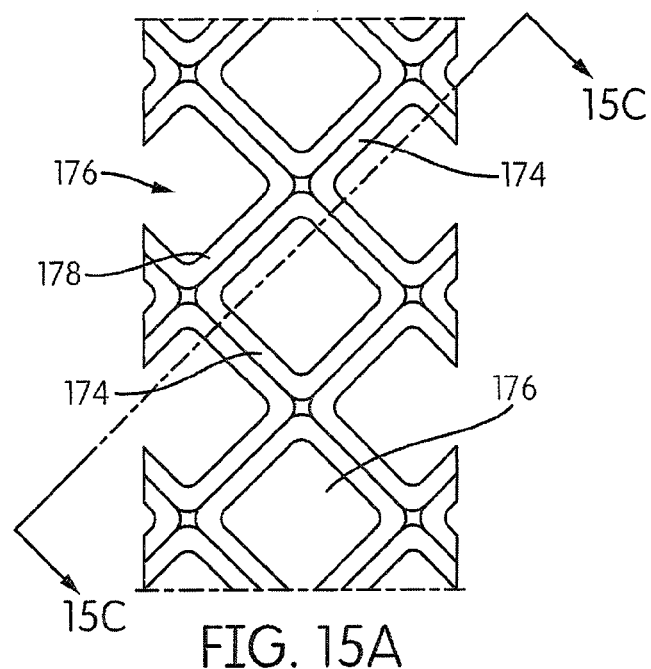
FIG. 15A is a partial top view of the exterior surface of the patterned portion of the sheet material. The exterior surface having angled channels therefrom. The angled portions may be configured as another cutting surface in additions to the channels edges.
Figure 15B:
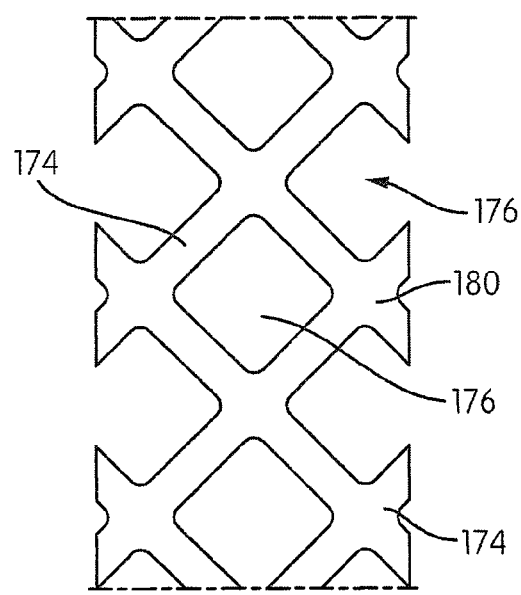
FIG. 15B is a partial top view of the exterior surface of the patterned portion of the sheet material. The channel portions having a generally flat interior surface.
Figure 15C:
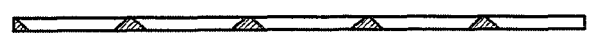
FIG. 15C. is a cross-sectional view of the embodiment shown in FIG. 15A showing the triangular cross-section of the channels.
Figure 16:
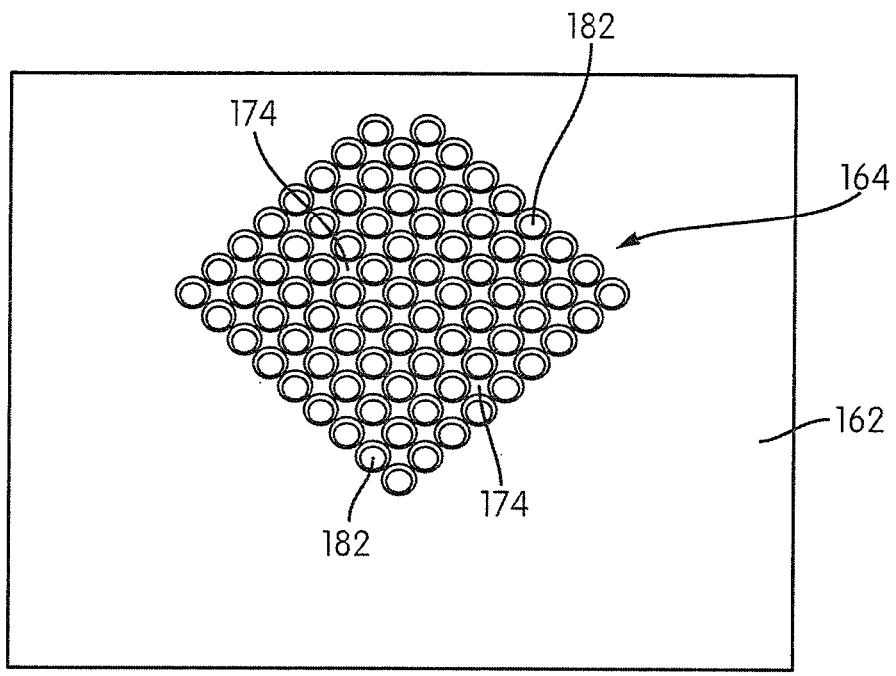
FIGS. 16-21 are top views of various sheet materials having different patterns using in the process shown in FIGS. 14A-14D.
Figure 17:
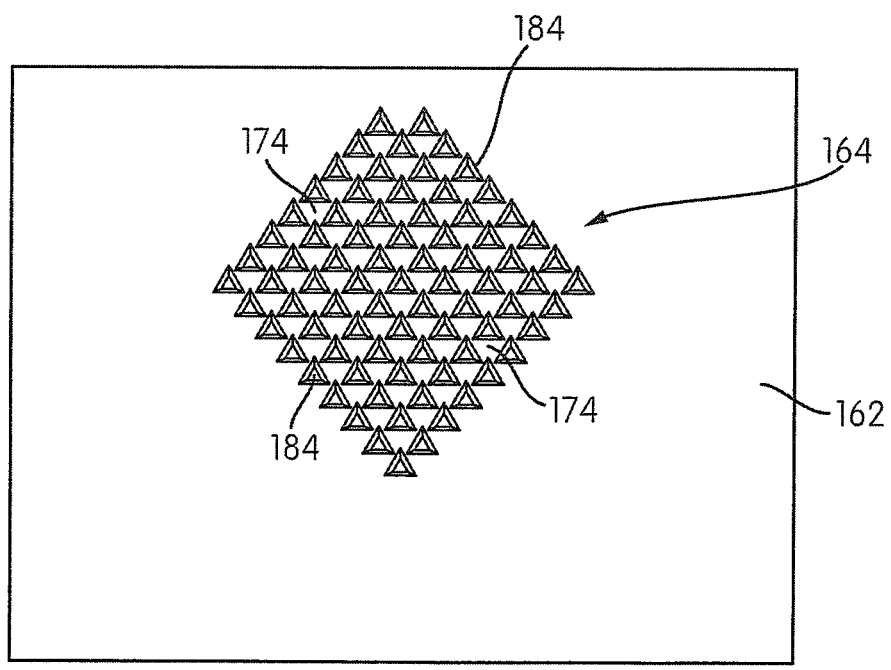
Figure 18:
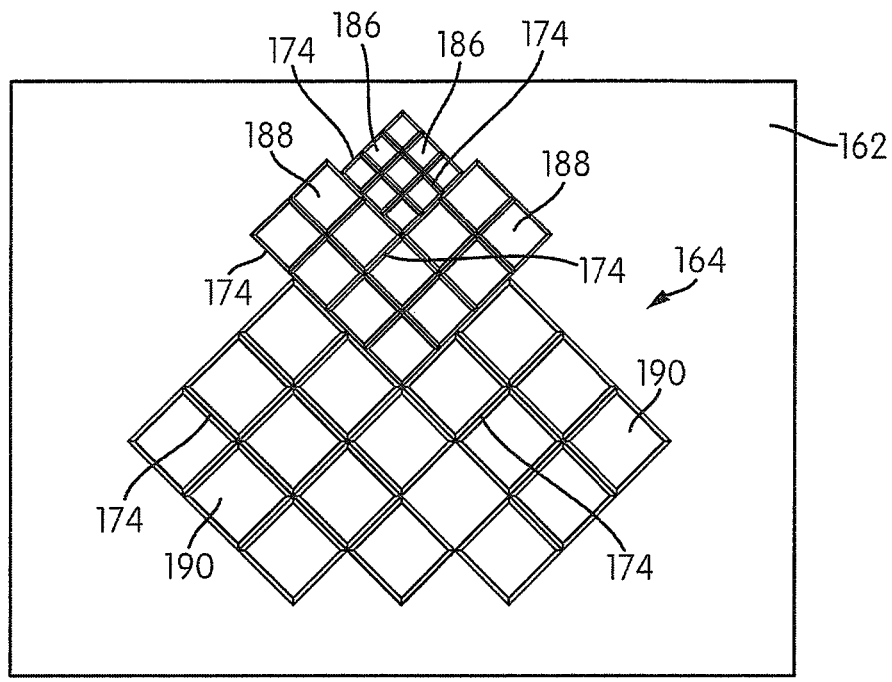
Figure 19:
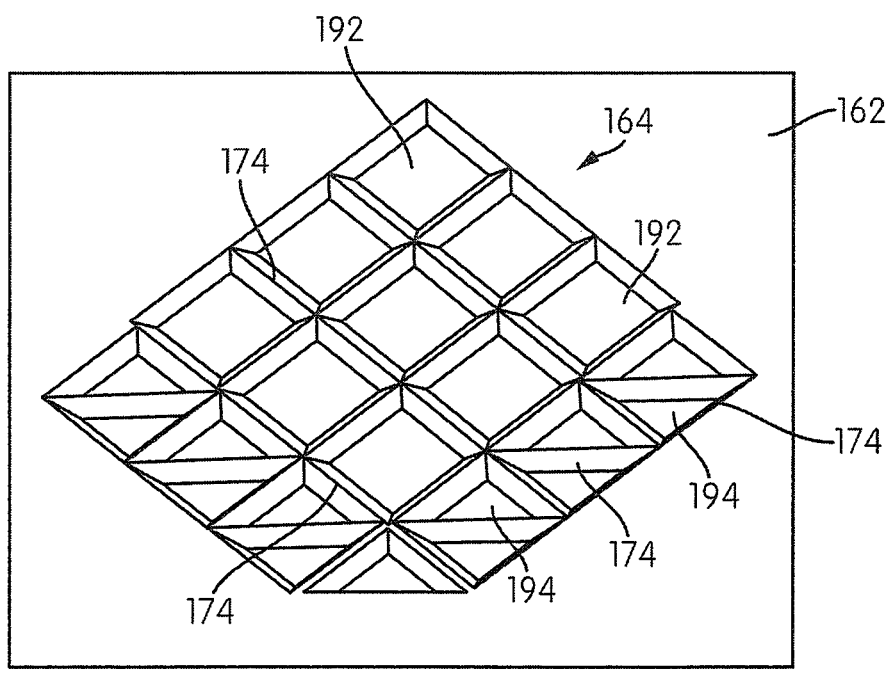
Figure 20:
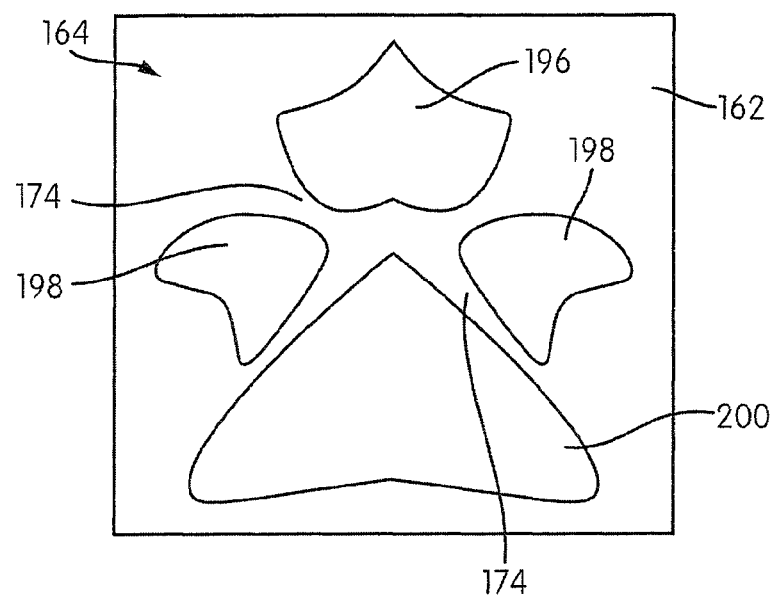
Figure 21:
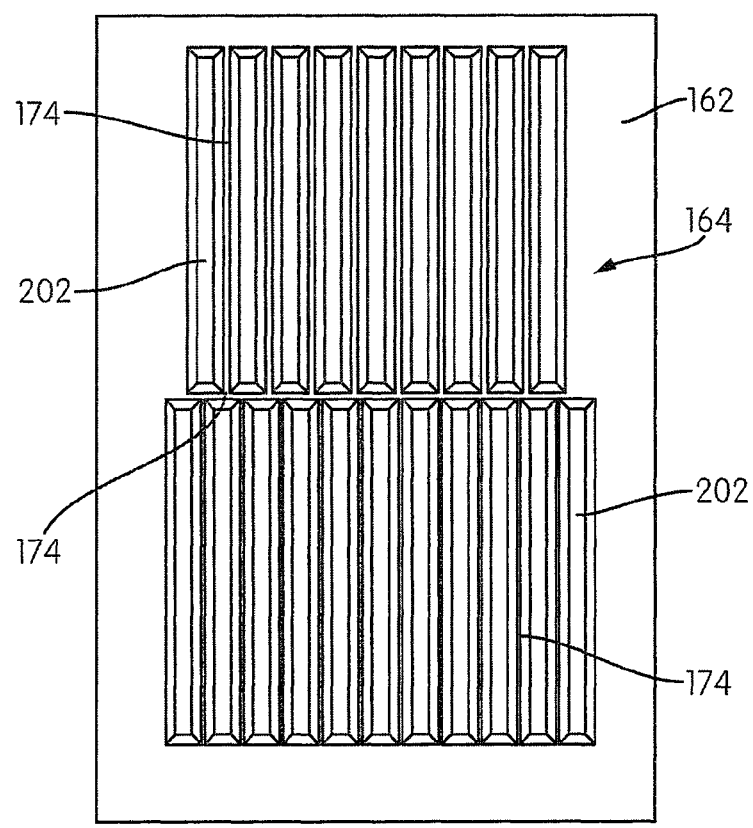

The present invention may provide another embodiment including the hollow instrument 170 formed from the process described above. The hollow instrument 170 may include a matrix 172 generally defined by the predetermined pattern 164. The matrix 172 may include channels 174 defining openings 176 having a diamond (e.g., square) shaped pattern. In one specific example, the channels 174 include an angled exterior surface 178 and a generally flat interior surface 180 as shown in FIGS. 15A-15C. It is appreciated that the exterior surface and/or the interior surface may have a slight curve resulting from the overall hollow shape (e.g., tubular cone shape) of the hollow instrument. Desirably, the cross-section of the channels 166 may be generally triangularly shaped, though not required.

FIGS. 16-21 will now be discussed. Various patterns may be chemically milled into the sheet material 162 thereby forming openings having circle shapes 182 (FIG. 16), triangle shapes 184 (FIG. 17), similar shapes (e.g., square, diamond, or otherwise shapes) of different sizes 186,188, 190 (FIG. 18), a plurality of shapes including a plurality of similarly sized first shapes 192 (e.g., squares or otherwise) and a plurality of similarly sized second shapes 194 (e.g., triangles or otherwise), the first shapes 192 being different from the second shapes 194 (FIG. 19), different shapes of various sizes 196,198,200 (FIG. 20), elongated rectangle shapes 202 (FIG. 21), or otherwise, and any combination thereof.

The sheet material and/or the perimeter wall defining the hollow tube may include a contact thickness or a variable thickness. When included, the thickness may vary such the hollow instrument may have a thicker perimeter wall at the proximal end relative to the tip end or a thinner perimeter wall at the proximal end relative to the tip end, It is contemplated that the perimeter wall may include a variable thickness with a constant taper. Preferably the perimeter wall includes a contact thickness at least throughout the shaft portion of the hollow instrument.

It is appreciated that as the hollow instrument rotates, reciprocates and/or axially moves, its cross-sectional shape may be constantly changing to conform to the shape of the canal wall and the length of the circumference of the device in that plane may be constantly increasing as material is removed from the wall. This is to be compared to the situation with existing files in which the shape of the canal is changed to conform to the shape of the file and the files must constantly be replaced with files of larger diameter in order to clean, widen, and shape the canal.

The advantages to this new type of rotary hollow file design as compared to conventional rotary solid files may be that the new design may change geometry when forces are exerted upon it. This may allow for optimum cleaning and shaping of the root canal. Since most root canals are not exactly conic in shape, typically the dentist will either have to remove more of the dental structure than desired to ensure that they have removed all of the bacteria or will remove less than desired to preserve the root structure but this will not allow all of the bacteria to be removed. This design takes it a step further though in its development for three main reasons. The present invention may utilize an alternative process called Photochemical Machining (also known as Photochemical milling or Photo etching). The process includes fabricating sheet metal components using a photoresist (light sensitive material) and etchants to corrosively machine away selected areas. One of the main benefits to Photochemical machining may be that the tooling is inexpensive and quickly produced and it can make a part in hours after receiving the drawing. Furthermore, it is appreciated that the Photochemical machining process may allow for a variable cross-section. With Photochemical machining, it allows for a variable cross-section where one side is aggressive for cutting while the other side is wider and not aggressive for structure stability.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed:

1. A method for manufacturing a hollow endodontic rotary file useful for shaping and cleaning root canals, comprising the steps of:
    a. providing a hollow tube extending along a longitudinal tube axis, the hollow tube having a proximal end and a shaft portion with a tip;
    b. forming a plurality of longitudinal tapered openings along the shaft portion of the hollow tube following a predetermined pattern that extend to the tip thereby defining a plurality of tapered fingers, therebetween, each finger having an outer surface and an inner surface extending between longitudinal opposing edges that extend to a tip end at the tip of the hollow tube, the opposing edges tapering towards one another so that each finger is wider towards the direction of the proximal end and narrower towards the tip; and
    c. deforming at least a portion of the hollow tube into a desired shape; and
    d. sharpening a portion of at least one of the longitudinal opposing edges to provide a cutting edge;
    e. joining at least two tapered fingers along a portion of at least one tapered opening to secure the hollow tube in the desired shape thereby forming the hollow endodontic rotary file;
    wherein each tip of the plurality of fingers or a portion proximate to each tip of the plurality of tapered fingers are deformed towards one another and converge towards the tube axis so that the shaft portion has a smaller outer diameter near the tip than at other portions of the shaft portion thereby forming a circumferential tapered shaft portion.

2. The method of claim 1, wherein the plurality of tapered openings are formed along the shaft portion of the hollow tube defining at least three tapered fingers radially spaced from the tube axis.

3. The method of claim 2, wherein a first longitudinal tapered opening extends between a first finger and a second finger, a second longitudinal tapered opening extends between the second tapered finger and a third tapered finger, and a third longitudinal tapered opening extends between the third tapered finger and the first tapered finger.

4. The method of claim 3, wherein each of the at least two tapered fingers include an end portion, the end portions being brought into contact during the deforming step to forming a tip of the tapered shaft portion.

5. The method of claim 3, wherein during the joining step, the first tapered finger is joined to the second tapered finger through a portion of the first longitudinal tapered opening by at least one binding, the second tapered finger is joined to the third tapered finger through a portion of the second longitudinal tapered opening by at least one binding, and the third tapered finger is joined to the first tapered finger through a portion of the third longitudinal tapered opening by at least one binding.

6. The method of claim 4, wherein each of the at least two tapered fingers are joined to an adjacent tapered finger through at least one of the plurality of longitudinal tapered openings by at least one binding at the tip of the tapered shaft portion.

7. The method of claim 5, wherein a plurality of bindings join at least two of the first tapered finger, the second tapered finger and the third tapered finger through at least one of the first longitudinal tapered opening, the second longitudinal tapered opening, and the third longitudinal tapered opening.

8. The method of claim 1, wherein at least one tapered finger includes a plurality of boss portions.

9. The method of claim 1, further comprising the step of coating or bonding abrasive material to an external surface of the hollow endodontic rotary file useful for shaping and cleaning root canals.

10. A method for manufacturing a hollow endodontic rotary file useful for shaping and cleaning root canals, comprising the steps of:
    a. providing a sheet of material;
    b. chemically milling the sheet to form a plurality of openings by removing material following a predetermined pattern, the milled sheet having at least two opposing tapered edges;
    c. rolling the milled sheet into a desired tubular geometry;

d. sharpening at least a portion of the plurality of openings to provide a cutting edge; and e. joining a portion of the at least two opposing edges to secure the desired tubular geometry;

wherein prior to or after step b, the at least two opposing edges are sloped towards one another such that upon joining the at least two opposing edges, a tapered hollow endodontic rotary file, instrument is formed having a shaft portion and a tip; and wherein the tapered hollow endodontic rotary file converges towards the tip such the a first diameter at the tip is smaller than a second diameter along the shaft portion; and wherein the predetermined pattern includes a variable groove having curves of decreasing amplitude.

11. The method of claim 10, further comprising the step of cutting the milled sheet to a desired shape.

12. The method of claim 10, wherein the chemically milling step is accomplished by photochemical machining.

13. The method of claim 10, wherein the predetermined pattern defines a matrix formed of the plurality of openings that are at least partially bound by channels having an angled exterior surface.

\* \* \* \* \*